(12) United States Patent
Henry et al.

(10) Patent No.: US 6,984,661 B2
(45) Date of Patent: Jan. 10, 2006

(54) UREA LINKER DERIVATIVES FOR USE AS PPAR MODULATORS

(75) Inventors: James Robert Henry, Indianapolis, IN (US); YiHong Li, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 40 days.

(21) Appl. No.: 10/500,489

(22) PCT Filed: Jan. 21, 2003

(86) PCT No.: PCT/US03/00034

§ 371 (c)(1),
(2), (4) Date: Jun. 29, 2004

(87) PCT Pub. No.: WO03/066581

PCT Pub. Date: Aug. 14, 2003

(65) Prior Publication Data

US 2005/0004183 A1 Jan. 6, 2005

Related U.S. Application Data

(60) Provisional application No. 60/354,438, filed on Feb. 5, 2002.

(51) Int. Cl.
| | |
|---|---|
| A61K 31/36 | (2006.01) |
| A61K 31/195 | (2006.01) |
| C07D 317/44 | (2006.01) |
| C07C 323/63 | (2006.01) |
| C07C 275/28 | (2006.01) |

(52) U.S. Cl. ............. 514/466; 514/562; 514/563; 514/564; 514/566; 562/439; 562/431; 549/439

(58) Field of Classification Search ............. 514/466, 514/562, 563, 564, 566; 562/439, 431; 549/439
See application file for complete search history.

(56) References Cited

U.S. PATENT DOCUMENTS

| | | | |
|---|---|---|---|
| 4,387,106 A | 6/1983 | De Vries et al. | |
| 4,465,509 A | 8/1984 | Takematsu et al. | |
| 6,706,744 B2 * | 3/2004 | Madsen et al. ............. | 514/367 |

FOREIGN PATENT DOCUMENTS

| | | |
|---|---|---|
| DE | 14 57 876 | 5/1969 |
| WO | WO 01 12187 | 2/2001 |
| WO | WO 01 60807 | 8/2001 |

OTHER PUBLICATIONS

CA 'Online!: Chemical Abstracts Service, Columbus, OH, US; Sato, et al.,: "*Urea Group–Containing Carboxylic Acids and Hypoglycemic and/or Hypolipidemic Agents Containing Them*"; retrieved from STN database accession No. 137:87463, XP0022411118, abstract & JP 2002 201171 A (Toa Eiyo, Ltd., Japan) Jul. 15, 2002.

WPI/Derwent Online; XP002241120; Database Accession No. an 1999–229131 '19!; Abstract & WO 00 12534 A (Univ. Northeastern Ohio) Mar. 9, 2000, abstract; pp. 23–29, 34, 36, 37.

Raju, B., et al.: "*Solution–phase Combinatorial synthesis of Ureas Using Nitrophenylcarbamates*"; BioOganic & Medicinal Chemistry Letters, Oxford, GB; vol. 8, No. 21, Nov. 3, 1998, pp. 3043–3048, XP004141872; ISSN: 0960–894X (scheme 1, compound type 7; table 1).

Nefzi, A., et al.: "*An Efficient Two–Step Synthesis of Mono–, Di– and Triureas from Resin–bound Amides*"; Tetrahedron Letters, Elsevier Science Publishers, Amsterdam, NL; vol. 40, No. 29, Jul. 15, 2000, pp. 5441–5446, XP0042094891, ISSN: 0040–4039 (compounds type 3, table 1).

Ishii, et al.: "*Highly Selective Aldose Reductase Inhibitors 1,3–(Arylalkyl)–2, 4, 5–Trioxoimidazolidine–I–Asetic Acids*";Journal of Medicinal Chemistry, American Chemical Society, Washington, US; vol. 39, No. 9, (1996), pp. 1924–1927, XP002064894, ISSN: 0022–2623.

Tanka, et al.: "*Inhibitors of Acyl–CoA;Cholesterol O–Acyltransferase (ACAT), Part I: Identification and Structure–Activity Relationships of a Novel Series of Substituted N–Alkyl–N–Biphenylmethyl–N'–Arylcureas*"BioOrganic and Medicinal Chemistry, vol. 6, 1998, pp. 15–30, XP002241118(the whole document).

Crossfire Beilstein 'Online!: Beilstein Institut zur Förderung der Chemischen Wissenschaften, Frankfurt am Main, De; retrived from Beilstein, accession No. brn 2890655, XP002241121; Abstract & Vowinkel; Gleichenhagen: Tetrahedron Lett., 1974, pp. 143–146.

(Continued)

Primary Examiner—Peter O'Sullivan
(74) Attorney, Agent, or Firm—McCharri Vorndran-Jones

(57) ABSTRACT

The present invention is directed to compounds of the structural formula (I), and pharmaceutically acceptable salts, solvates and hydrates thereof: Formula I (a) R1, R2 and R6 are each independently selected from the group consisting of hydrogen, $C_1$–$C_8$ alkyl substituted $C_1$–$C_8$ alkyl, aryl-$C_{0-4}$-alkyl, substituted aryl-$C_{0-4}$-alkyl, heteroaryl-$C_{0-4}$-alkyl, substituted heteroaryl-$C_{0-4}$-alkyl, $C_3$–$C_6$ cycloalkylaryl-$C_{0-2}$-alkyl, and substituted $C_3$–$C_6$ cycloalkylaryl-$C_{0-2}$-alkyl; (b) X is an optionally substituted $C_1$–$C_5$ alkylene linker wherein one carbon atom of the linker may be replaced with O, NH or S; (c) Y is C, O, S, NH or a single bond; and (d) E is selected from the group consisting of hydrogen, C(R3)(R4)A, A, $(CH_2)_n$ COOR19 and substituted $(CH_2)_n$ COOR19.

(I)

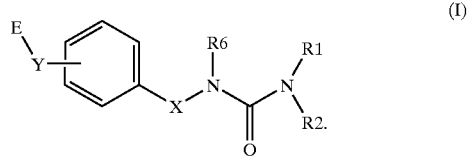

16 Claims, No Drawings

OTHER PUBLICATIONS

Crossfire Beistein 'Online!: Beilstein Institut zur Förderung der Chemischen Wissenschaften, Frankfurt am Main, DE; retrieved from Beilstein, accession No. brn 3271886, XP002241122; Abstract & Lohman: Chem. Ber., vol. 24m 1891, p. 2635.

Crossfire Beilstein 'Online!: Beilstein Institut zur Förderung der Chemischen Weissenschaften, Frankfurt am Main, DE; retrived from Beilstein, accession No. brn 3530969, XP002241123, abstract & Gabriel; Chem. Ber., vol. 47, 1914, p. 3030.

Crossfire Beilstein 'Online!: Beilstein Institut zur Förderung der Chemischen Wissenschaften, Frankfurt am Main, DE; retrieved from Beilstein, accession No. brn 2451140; XP002241124; abstract & Spinzl, M., et al.: Tetrahedron Lett., vol. 5, 1969, pp. 289–292.

Crossfire Beilstein 'Online!: Beilstein Institut zur Förderung der Chemischen Wissenschaften, Frankfurt am Main, DE; retrived from Beilstein, accession No. brn 247670, XP002241125, abstract & Koelzer and Wehr: Arzneim. Forsch., vol. 9, 1959, pp. 113–116.

Crossfire Beilstein 'Online!: Beilstein Institut zur Förderung der Chemischen Wissenschaften, Frankfurt am Main, DE; retrieved from Beilstein, accession No. brn 2812220, XP002241126, abstract & Adcock; Lawson: J. Chem. Soc C., 1996, pp. 65–67.

Crossfire Beilstein 'Online!: Beilstein Institut zur Förderung der Chemischen Wissenschaften, Frankfurt am Main, DE; retrieved from Beilstein, accession No. brn 3272124; XP002241127, abstract & Schoeberl; Kawohl: Monatsh. Chem., vol. 88, 1957, pp. 478–492.

Crossfire Beilstein 'Online!: Beilstein Institut zur Förderung der Chemischen Wissenschaften, Frankfurt am Main, DE; retrieved from Beilstein, accession No. brn 3271854, XP002241128, abstract & Goldenring: Chem. Ber., No. 23, 1890, p. 1173.

Crossfire Beilstein 'Online!: Beilstein Institut zur Förderung der Chemischen Wissenschaften, Frankfurt am Main, DE; retrieved from Beilstein, accession No. brn 2860895, XP002241129, abstract & Van Alphen: Recl. Trav. Chim. Pays–Bas, vol. 54, 1935, p. 885.

Papesch, et al: "*Synthesis of 1–mono– and 1,3–di–substituted 6–aminouracils, Diuretic Activity*"; Journal of Organic Chemistry, American Chemical Society, Easton, US, XP002156529, ISSN: 0022–3263, (table I, the last entry and p. 1887, experimental).

Davies, et al.: "*Intramolecular Cyclisation of 2–Phenylethyl Isocyanates*"; J. Chem. Soc., Perkin Trans. 1, 1978, pp. 180–184, XP009010939 (compound 13).

Dimmock, et al.: "*Ureylene Anticonvulsants and Related Compounds*": Pharmazie, vol. 55, No. 7, (2000), pp. 490–494, XP001157470 (compounds type 1 and table 1, p. 491).

Skinner, et al.: "*N–substituted N'–Phenylureas*"; J. Org. Chem., vol. 25, 1960, pp. 2046–2047, XP00241235 (table 1).

* cited by examiner

UREA LINKER DERIVATIVES FOR USE AS PPAR MODULATORS

This Application claims the benefit of U.S. Provisional Application Ser. No. 60/354,438, filed 5 Feb. 2002, and PCT Application Ser. No. PCT/US03/00034, filed 21 Jan. 2003.

BACKGROUND OF THE INVENTION

Peroxisome Proliferator Activated Receptors (PPARs) are members of the nuclear hormone receptor super family, which are ligand-activated transcription factors regulating gene expression. Various subtypes of PPARs have been discovered. These include, for example, PPARα, NUC1, PPARγ and PPARδ.

The PPARα receptor subtypes are reported to be activated by medium and long-chain fatty acids. They are involved in stimulating beta-oxidation of fatty acids and with the activity of fibrates which reportedly produce a substantial reduction in plasma triglycerides and moderate reduction in low density lipoprotein (LDL) cholesterol.

PPARα, PPARγ and PPARδ receptors have been implicated in diabetes mellitus, cardiovascular disease, obesity, Syndrome X and gastrointestinal disease, such as, inflammatory bowel disease. Syndrome X is the combination of symptoms which include hyperinsulemia combined with hypertension, elevated body weight, elevated triglycerides and elevated LDL.

A need exists for new pharmaceutical agents which affect, treat or prevent cardiovascular disease, particularly that associated with Syndrome X, while preventing or minimizing weight gain, and more preferably while improving insulin sensitivity.

SUMMARY OF THE INVENTION

The present invention is directed to compounds represented by the following structural formula:

Formula I

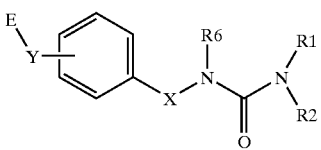

and pharmaceutically acceptable salts, solvates and hydrates thereof, wherein:
(a) R1, R2 and R6 are each independently selected from the group consisting of hydrogen, $C_1$–$C_8$ alkyl, substituted $C_1$–$C_8$ alkyl, aryl-$C_{0-4}$-alkyl, substituted aryl-$C_{0-4}$-alkyl, $C_3$–$C_6$ cycloalkyl, substituted $C_3$–$C_6$ cycloalkyl, heteroaryl-$C_{0-4}$-alkyl, substituted heteroaryl-$C_{0-4}$-alkyl, $C_3$–$C_6$ cycloheteroalkylaryl-$C_{0-2}$-alkyl, substituted $C_3$–$C_6$ cycloheteroalkylaryl-$C_{0-2}$-alkyl, $C_3$–$C_6$ cycloalkylaryl-$C_{0-2}$-alkyl and substituted $C_3$–$C_6$ cycloalkylaryl-$C_{0-2}$-alkyl; wherein the substituents for said substituted alkyl, arylalkyl, cycloalkyl, heteroarylalkyl, cycloheteroalkylarylalkyl, and cycloalkylarylalkyl are from one to three substituents each independently selected from R1';
(b) R1', R3', R4' and R19' are each independently selected from the group consisting of H, $C_1$–$C_5$ alkyl, $C_1$–$C_5$ alkoxy, $C_1$–$C_5$ haloalkyl, $C_1$–$C_5$ haloalkoxy, nitro, cyano, CHO, hydroxyl, aryl$C_0$–$C_{5}$alkoxy, aryl$C_0$–$C_{5}$alkyl, alkylcarboxamido and COOH;
(c) X is an optionally substituted $C_1$–$C_5$ alkylene linker wherein one carbon atom of the linker may be replaced with O, NH or S;
(c) Y is C, O, S, NH or a single bond; and
(d) E is selected from the group consisting of hydrogen, C(R3) (R4)A, A, and $(CH_2)_n$ COOR19; wherein said $(CH_2)_n$ COOR19 is optionally substituted with a group selected from $C_1$–$C_5$ alkyl, aryl$C_0$–$C_5$alkoxy, and aryl$C_0$–$C_5$alkyl; and wherein
(i) n is 0, 1, 2 or 3,
(ii) A is selected from the group consisting of carboxyl, $C_1$–$C_3$alkylnitrile, carboxamide, sulfonamide, substituted sulfonamide, acylsulfonamide, substituted acylsulfonamide, tetrazole and substituted tetrazole;
(iii) R3 is selected from the group consisting of H, $C_1$–$C_5$ alkyl, and $C_1$–$C_5$ alkoxy, wherein said alkyl and alkoxy are each optionally substituted with from one to three substituents each independently selected from R3';
(iv) R4 is selected from the group consisting of H, halo, $C_1$–$C_5$ alkyl, $C_1$–$C_5$ alkoxy, $C_3$–$C_6$ cycloalkyl, aryl $C_0$–$C_4$ alkyl, and aryl$c_0$–$C_2$alkoxy, or R3 and R4 are optionally combined to form a $C_3$–$C_4$ cycloalkyl, and wherein said alkyl, alkoxy, cycloalkyl, arylalkyl, and arylalkoxy are each optionally substituted with from one to three substituents each independently selected from R4'; and
(e) R19 is selected from the group consisting of hydrogen, arylmethyl, and $C_1$–$C_4$alkyl, wherein said arylmethyl and $C_1$–$C_4$alkyl, are each optionally substituted with from one to three substituents each independently selected from R19'.

One preferred embodiment of this invention is a compound and pharmaceutically acceptable salts, solvates and hydrates of Structural Formula:

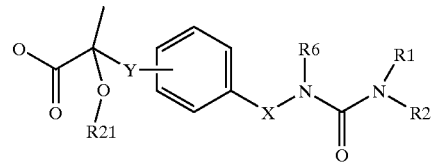

wherein R21 is selected from the group consisting of phenyl, substituted phenyl, and $C_1$–$C_6$ alkyl.

Another preferred embodiment is a compound and pharmaceutically acceptable salts, solvates and hydrates of Structural Formula:

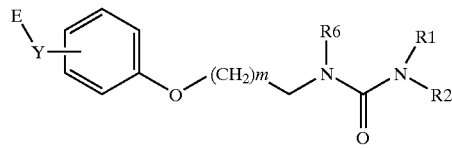

wherein m is 0, 1, or 2.

Another preferred embodiment is a compound of the formula:

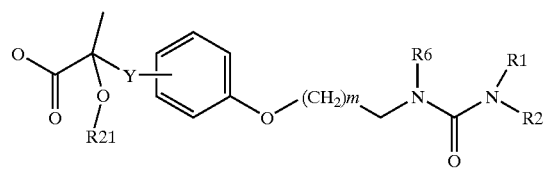

wherein m is 0, 1, or 2.

In another feature of this invention, a compound claimed herein is radiolabeled.

In one embodiment, the present invention also relates to pharmaceutical compositions which comprising at least one compound of the present invention, or a pharmaceutically acceptable salt, solvate, or hydrate thereof, and a pharmaceutically acceptable carrier.

In another embodiment, the present invention relates to a method of modulating a PPAR alpha receptor by contacting the receptor with at least one compound represented by Structural Formula I, and pharmaceutically acceptable salts, solvates and hydrates thereof.

In another embodiment, the present invention relates to a method of modulating a PPAR gamma receptor by contacting the receptor with at least one compound represented by Structural Formula I, and pharmaceutically acceptable salts, solvates and hydrates thereof.

In another embodiment, the present invention relates to a method of modulating a PPAR alpha receptor and a PPAR gamma receptor by contacting the receptor with at least one compound represented by Structural Formula I, and pharmaceutically acceptable salts, solvates and hydrates thereof.

The compounds of the present invention and pharmaceutically acceptable salts, solvates and hydrates thereof can be effective in treating and, in patients susceptible thereto, preventing, Syndrome X, Type II diabetes, hyperglycemia, hyperlipidemia, obesity, coagaulopathy, hypertension, atherosclerosis, and other disorders related to Syndrome X and cardiovascular diseases. In addition, the compounds are expected to be associated with fewer side effects than compounds currently used to treat these conditions. Further, compounds of this invention can be useful for lowering fibrinogen, increasing HDL levels, treating renal disease, controlling desirable weight, treating demyelinating diseases, treating certain viral infections, and treating liver disease.

DETAILED DESCRIPTION OF THE INVENTION

The terms used to describe the instant invention have the following meanings herein.

As used herein, alkyl groups include straight chained or branched hydrocarbons having the indicated number of carbons. Such alkyl group is completely saturated. The when branched, for example, the alkyl can be primary, secondary or tertiary.

As used herein, alkylene linker is an optionally unsaturated $C_1-C_5$ straight or branched chain hydrocarbon group.

As used herein the term "haloalkyl" means at least one halo attached to the alkyl. The term includes, for example, $CF_3$, $(CH_2)_2CF_3$, and $CCl$. It is preferred that the alkyl is $C_1-C_3$ alkyl. It can be especially preferred that the alkyl in haloalkyl is $C_1$. Halo includes Cl, Br, F, and I. It may be preferred that halo is F. It can be preferred for certain embodiments of this invention that haloalkyl is $CF_3$.

Cycloalkyl groups, as used herein, include cyclic hydrocarbons, which are partially or completely saturated. It is generally preferred that the cycloalkyl groups are completely saturated.

As used herein, aryl groups include carbocyclic aromatic ring systems (e.g. phenyl), fused polycyclic aromatic ring systems (e.g. naphthyl and anthracenyl) and aromatic ring systems fused to carbocyclic non-aromatic ring systems (e.g., 1,2,3,4-tetrahydronaphthyl and benzodioxyl). A preferred aryl can be phenyl or naphthyl. An especially preferred aryl can be phenyl.

Heterocyclic group, as used herein, is a ring system having at least one heteroatom such as nitrogen, sulfur or oxygen. Heterocyclic groups include benzofuranyl, benzothiazolyl, benzothienyl, isoquinolyl, isoxazolyl, morpholino, oxadiazolyl, pyridyl, pyrimidinyl, pyrrolyl, quinolyl, tetrahydropyranyl and thienyl.

As used herein, aryl-$C_{0-4}$-alkyl, means an aryl linked to the parent molecule through an alkyl having the indicated number of carbon. When the alkyl is $C_0$-alkyl, the term means that the aryl is directly bonded to the parent molecule. The term means, for example, but not limited to, benzyl, phenyl, phenylalkyl, naphthyl, and naphthylalkyl. It can be preferred that arylalkyl is selected from phenyl and benzyl.

Likewise, the term arylalkoxy means that the aryl is linked to the parent molecule through a carboxy having the indicated number of carbon. When arylalkoxy is arylcoalkoxy then the term means aryloxy, with no carbon in the link. It can be preferred that arylalkyloxy is aryl$C_1-C_2$alkyloxy. It can be preferred that the term is arylcoalkyloxy.

The term heteroaryl-$C_{0-4}$-alkyl, means that a heteroaryl is linked to the parent molucule through an alkyl having the indicated number of carbon.

The term $C_3-C_6$ cycloheteroalkylaryl-$C_{0-2}$-alkyl, refers to a fused ring system linked to the parent molecule through the alkyl. The fused ring system is a heterocyclic ring fused to an aryl and is, for example but not limited to,

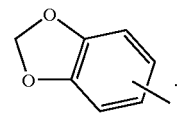

Likewise, the term $C_3-C_6$ cycloalkylaryl-$C_{0-2}$-alkyl refers to a fused ring system that comprises a cycloalkyl fused with an aryl and linked to the parent molecule through the alkyl.

Examples of suitable substituents for an "optionally substituted $C_2-C_5$ alkylene linker", include one or more independently selected from the group consisting of $C_1-C_6$alkyl, oxo, substituted or unsubstituted aryl$C_0-C_3$alkyl, $C_1-C_3$alkoxy, hydroxy, $C_3-C_6$cycloalkyl and halo. When the alkylene linker is substituted, it is preferred that there are from one to three independent substitutions.

Examples of suitable substituents for a substituted $C_1-C_3$ alkylene, include one or more independently selected from the group consisting of $C_1-C_6$alkyl, oxo, aryl $C_0-C_3$alkyl, $C_1-C_3$alkoxy, hydroxy, and halo. When the alkylene is substituted it is preferred that there are from 1–3 independent substitutions.

Examples of suitable substituents for A groups, wherein the A is a sulfonamide, include one or more independently selected from the group consisting of $C_1-C_4$ alkyl, $C_1-C_4$ haloalkyl, heteroaryl, and aryl. When the A group is substituted, it is preferred that there are from 1–3 independent substitutions on the A group.

Examples of suitable substituents for A groups, wherein A is acylsulfonamide or tetrazole include, for example, one or more independently selected from $C_1-C_4$ alkyl, $C_1-C_4$ haloalkyl, substituted or unsubstituted heteroaryl, or substituted or unsubstituted aryl. It is preferred that when A is substituted, there are from one to three independently selected substituents.

Preferably, for the compounds of the present invention, represented by Structural Formula I, and with their respective pharmaceutical compositions, X contains an oxygen.

The compounds of Structural Formula I may contain one or more chiral centers, and exist in different optically active forms. When compounds of Structural Formula I contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound represented by Structural Formula I has more than one chiral substituent it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds of Structural Formula I and mixtures thereof.

Certain compounds of Structural Formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Structural Formula I and mixtures thereof.

Certain compounds of Structural Formula I may exist in zwitterionic form and the present invention includes each zwitterionic form of compounds of Structural Formula I and mixtures thereof.

Certain compounds of Structural Formula I and their salts may also exist in the form of solvates and hydrates, and the present invention includes each solvate and mixtures thereof.

"Pharmaceutically-acceptable salt" refers to salts of the compounds of the Structural Formula I that are substantially non-toxic to mammals. Typical pharmaceutically-acceptable salts include those salts prepared by reaction of the compounds of the present invention with a mineral or organic acid or an organic or inorganic base. Such salts are known as base addition salts, respectively. It should be recognized that the particular counterion forming a part of any salt of this invention is not of a critical nature, so long as the salt as a whole is pharmaceutically-acceptable and as long as the counterion does not contribute undesired qualities to the salt as a whole.

By virtue of its acidic moiety, a compound of Structural Formula I forms salts with pharmaceutically acceptable bases. Some examples of base addition salts include metal salts such as aluminum; alkali metal salts such as lithium, sodium or potassium; and alkaline earth metal salts such as calcium and magnesium; and ammonium or substituted ammonium salts. Examples of substituted ammonium salts include, for instance, those with lower alkylamines such as trimethylamine, triethylamine; hydroxyalkylamines such as 2-hydroxyethylamine, bis-(2-hydroxyethyl)-amine or tri-(2-hydroxyethyl)-amine, cycloalkylamines such as bicyclohexylamine or dibenzylpiperidine, N-benzyl-β-phenethylamine, dehydroabietylamine, N,N'-bisdehydroabietylamine, glucamine, N-methylglucamine; bases of the pyridine type such as pyridine, collidine, quinine or quinoline; and salts of basic amino acids such as lysine and arginine.

These salts may be prepared by methods known to those skilled in the art.

In addition, it is generally not desirable to formulate pharmaceuticals containing substantial amounts of organic solvent (e.g., ethyl acetate) due to potential solvent toxicity to the recipient thereof and changes in potency of the pharmaceutical as a function of the solvent. In addition, from a manufacturing perspective, it is also generally less desirable to prepare non-crystalline materials whenever said preparation involves a collection of the final product via filtration. Such filtrations are often more difficult to perform when the material collected is non-crystalline. Moreover, it is also generally less desirable, from a manufacturing perspective, to formulate pharmaceuticals containing substantial amounts of water (hydrates) because the level of hydration will typically be some function of the relative humidity at which the pharmaceutical is produced and stored. In other words, potency variability is typically more problematic with a hydrate relative to its anhydrous form. The present invention provides a desired crystalline form.

The term, "active ingredient" means the compounds generically described by Structural Formula I as well as the salts, solvates, and hydrates of such compounds.

The term "pharmaceutically acceptable" means that the carrier, diluent, excipients and salt must be compatible with the other ingredients of the composition, and not deleterious to the recipient thereof. Pharmaceutical compositions of the present invention are prepared by procedures known in the art using well known and readily available ingredients.

"Preventing" refers to reducing the likelihood that the recipient will incur or develop any of the pathological conditions described herein. It is preferred that the recipient is thought to be susceptible to said condition.

"Treating" refers to mediating a disease or condition and preventing, or mitigating, its further progression or ameliorate the symptoms associated with the disease or condition.

"Pharmaceutically-effective amount" means that amount of a compound, or of its salt, solvate, or hydrate thereof, that will elicit the biological or medical response of a tissue, system, or mammal. Such an amount can be administered prophylactically to a patient thought to be susceptible to development of a disease or condition. Such amount when administered prophylactically to a patient can also be effective to prevent or lessen the severity of the mediated condition. Such an amount is intended to include an amount which is sufficient to modulate a PPAR alpha receptor or to prevent or mediate a disease or condition. Conditions prevented or treated by PPARα receptors include diabetes mellitus, cardiovascular disease, Syndrome X, obesity and gastrointestinal disease.

A "mammal" is an individual animal that is a member of the taxonomic class Mammalia. The class Mammalia includes humans, monkeys, chimpanzees, gorillas, cattle, swine, horses, sheep, dogs, cats, mice, and rats.

Administration to a human is most preferred. The compounds and compositions of the present invention are useful for the treatment and/or prophylaxis of cardiovascular disease, for raising serum HDL cholesterol levels, for lowering serum triglyceride levels and for lower serum LDL cholesterol levels. Elevated triglyceride and LDL levels, and low HDL levels, are risk factors for the development of heart disease, stroke, and circulatory system disorders and diseases.

The compounds and compositions of the present invention are also useful for treating and/or preventing obesity.

Further, these compounds and compositions are useful for the treatment and/or prophylaxis of non-insulin dependent diabetes mellitus (NIDDM) with reduced or no body weight gains by the patients. Furthermore, the compounds and compositions of the present invention are useful to treat or prevent acute or transient disorders in insulin sensitivity, such as sometimes occur following surgery, trauma, myocardial infarction, and the like. The physician of ordinary skill will know how to identify humans who will benefit from administration of the compounds and compositions of the present invention.

The present invention further provides a method for the treatment and/or prophylaxis of hyperglycemia in a human or non-human mammal which comprises administering an effective, non-toxic amount of a compound of the general formula (I), or a tautomeric form thereof and/or a pharmaceutically acceptable salt thereof and/or a pharmaceutically acceptable solvate thereof to a hyperglycemic human or non-human mammal in need thereof.

They are useful as therapeutic substances in preventing or treating Syndrome X, diabetes mellitus and related endocrine and cardiovascular disorders and diseases in human or non-human animals.

The invention also relates to the use of a compound of Formula I as described above, for the manufacture of a medicament for treating a PPARα mediated condition.

A therapeutically effective amount of a compound of Structural Formula I can be used for the preparation of a medicament useful for treating Syndrome X, diabetes, treating obesity, lowering tryglyceride levels, lowering serum LDL levels, raising the plasma level of high density lipoprotein, and for treating, preventing or reducing the risk of developing atherosclerosis, and for preventing or reducing the risk of having a first or subsequent atherosclerotic disease event in mammals, particularly in humans. In general, a therapeutically effective amount of a compound of the present invention typically reduces serum triglyceride levels of a patient by about 20% or more, and increases serum HDL levels in a patient. Preferably, HDL levels will be increased by about 30% or more. In adition, a therapeutically effective amount of a compound, used to prevent or treat NIDDM, typically reduces serum glucose levels, or more specifically HbAlc, of a patient by about 0.7% or more.

Advantageously, compositions containing the compound of Structural Formula I or the salts thereof may be provided in dosage unit form, preferably each dosage unit containing from about 1 to about 500 mg be administered although it will, of course, readily be understood that the amount of the compound or compounds of Structural Formula I actually to be administered will be determined by a physician, in the light of all the relevant circumstances.

When used herein Syndrome X includes pre-diabetic insulin resistance syndrome and the resulting complications thereof, insulin resistance, non-insulin dependent diabetes, dyslipidemia, hyperglycemia obesity, coagulopathy, hypertension and other complications associated with diabetes. The methods and treatments mentioned herein include the above and encompass the treatment and/or prophylaxis of any one of or any combination of the following: pre-diabetic insulin resistance syndrome, the resulting complications thereof, insulin resistance, Type II or non-insulin dependent diabetes, dyslipidemia, hyperglycemia, obesity and the complications associated with diabetes including cardiovascular disease, especially atherosclerosis.

The compositions are formulated and administered in the same general manner as detailed herein. The compounds of the instant invention may be used effectively alone or in combination with one or more additional active agents depending on the desired target therapy. Combination therapy includes administration of a single pharmaceutical dosage composition which contains a compound of Structural Formula I and one or more additional active agents, as well as administration of a compound of Structural Formula I and each active agent in its own separate pharmaceutical dosage formulation. For example, a compound of Structural Formula I or thereof and an insulin secretogogue such as biguanides, thiazolidinediones, sulfonylureas, insulin, or α-glucosidose inhibitors can be administered to the patient together in a single oral dosage composition such as a tablet or capsule, or each agent administered in separate oral dosage formulations. Where separate dosage formulations are used, a compound of Structural Formula I and one or more additional active agents can be administered at essentially the same time, i.e., concurrently, or at separately staggered times, i.e., sequentially; combination therapy is understood to include all these regimens.

An example of combination treatment or prevention of atherosclerosis may be wherein a compound of Structural Formula I or salts thereof is administered in combination with one or more of the following active agents: antihyperlipidemic agents; plasma HDL-raising agents; antihypercholesterolemic agents, fibrates, vitamins, aspirin, and the like. As noted above, the compounds of Structural Formula I can be administered in combination with more than one additional active agent.

Another example of combination therapy can be seen in treating diabetes and related disorders wherein the compounds of Structural Formula I, salts thereof can be effectively used in combination with, for example, sulfonylureas, biguanides, thiazolidinediones, α-glucosidase inhibitors, other insulin secretogogues, insulin as well as the active agents discussed above for treating atherosclerosis.

The compounds of the present invention, and the pharmaceutically acceptable salts, solvates and hydrates thereof, have valuable pharmacological properties and can be used in pharmaceutical compositions containing a therapeutically effective amount of a compound of the present invention, or pharmaceutically acceptable salts, solvates or hydrates thereof, in combination with one or more pharmaceutically acceptable excipients. Excipients are inert substances such as, without limitation carriers, diluents, fillers, flavoring agents, sweeteners, lubricants, solubilizers, suspending agents, wetting agents, binders, disintegrating agents, encapsulating material and other conventional adjuvants. Proper formulation is dependent upon the route of administration chosen. Pharmaceutical compositions typically contain from about 1 to about 99 weight percent of the active ingredient which is a compound of the present invention.

Preferably, the pharmaceutical formulation is in unit dosage form. A "unit dosage form" is a physically discrete unit containing a unit dose, suitable for administration in human subjects or other mammals. For example, a unit dosage form can be a capsule or tablet, or a number of capsules or tablets.

A "unit dose" is a predetermined quantity of the active compound of the present invention, calculated to produce the desired therapeutic effect, in association with one or more pharmaceutically-acceptable excipients. The quantity of active ingredient in a unit dose may be varied or adjusted from about 0.1 to about 1000 milligrams or more according to the particular treatment involved.

The dosage regimen utilizing the compounds of the present invention is selected by one of ordinary skill in the medical or veterinary arts, in view of a variety of factors, including, without limitation, the species, age, weight, sex, and medical condition of the recipient, the severity of the condition to be treated, the route of administration, the level of metabolic and excretory function of the recipient, the dosage form employed, the particular compound and salt thereof employed, and the like.

Preferably, the compounds of the present invention are administered in a single daily dose, or the total daily dose may be administered in divided doses, two, three, or more times per day. Where delivery is via transdermal forms, of course, administration is continuous.

Suitable routes of administration of pharmaceutical compositions of the present invention include, for example, oral, eyedrop, rectal, transmucosal, topical, or intestinal administration; parenteral delivery (bolus or infusion), including intramuscular, subcutaneous, intramedullary injections, as well as intrathecal, direct intraventricular, intravenous, intraperitoneal, intranasal, or intraocular injections. The compounds of the invention can also be administered in a targeted drug delivery system, such as, for example, in a liposome coated with endothelial cell-specific antibody.

For oral administration, the compounds can be formulated readily by combining the active compounds with pharmaceutically acceptable carriers well known in the art. Such carriers enable the compounds of the invention to be formulated as tablets, pills, powders, sachets, granules, dragees, capsules, liquids, elixers, tinctures, gels, emulsions, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores.

For oral administration in the form of a tablet or capsule, the active ingredient may be combined with an oral, non-toxic, pharmaceutically-acceptable carrier, such as, without limitation, lactose, starch, sucrose, glucose, methyl cellulose, calcium carbonate, calcium phosphate, calcium sulfate, sodium carbonate, mannitol, sorbitol, and the like; together with, optionally, disintegrating agents, such as, without limitation, cross-linked polyvinyl pyrrolidone, maize, starch, methyl cellulose, agar, bentonite, xanthan gum, alginic acid, or a salt thereof such as sodium alginate, and the like; and, optionally, binding agents, for example, without limitation, gelatin, acacia, natural sugars, beta-lactose, corn sweeteners, natural and synthetic gums, acacia, tragacanth, sodium alginate, carboxymethyl-cellulose, polyethylene glycol, waxes, and the like; and, optionally, lubricating agents, for example, without limitation, magnesium stearate, sodium stearate, stearic acid, sodium oleate, sodium benzoate, sodium acetate, sodium chloride, talc, and the like. When a dosage unit form is a capsule, it may contain, in addition to materials of the above type, a liquid carrier such as a fatty oil.

Solid form formulations include powders, tablets and capsules. A solid carrier can be one or more substance which may also act as flavoring agents, lubricants, solubilisers, suspending agents, binders, tablet disintegrating agents and encapsulating material.

In powders, the carrier is a finely divided solid which is in admixture with the finely divided active ingredient. In tablets, the active ingredient is mixed with a carrier having the necessary binding properties in suitable proportions and compacted in the shape and size desired.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Sterile liquid formulations include suspensions, emulsions, syrups, and elixirs. The active ingredient can be dissolved or suspended in a pharmaceutically acceptable carrier, such as sterile water, sterile organic solvent, or a mixture of both sterile water and sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in a suitable oil.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

All formulations for oral administration should be in dosages suitable for such administration. Particularly suitable compositions for oral administration are unit dosage forms such as tablets and capsules.

For parental administration the compounds of the present invention, or salts thereof, can be combined with sterile aqueous or organic media to form injectable solutions or suspensions. Formulations for injection may be presented in unit dosage form, such as in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that each syringability exists. It must be stable under the conditions of manufacture and storage and must be preserved against any contamination. The carrier can be solvent or dispersion medium containing, for example, water, preferably in physiologically compatible buffers such as Hanks's solution, Ringer's solution, or physiological saline buffer, ethanol, polyol (e.g. glycerol, propylene glycol and liquid polyethylene glycol), propylene glycol and liquid polyethylene glycol), suitable mixtures thereof, and vegetable oils. Under ordinary conditions of storage and use, these preparations contain a preservative to prevent the growth of microorganisms.

The injectable solutions prepared in this manner can then be administered intravenously, intraperitoneally, subcutaneously, or intramuscularly, with intramuscular administration being preferred in humans.

For transmucosal administration, penetrants appropriate to the barrier to be permeated are used in the formulation. Such penetrants are generally known in the art. The active compounds can also be administered intranasally as, for example, liquid drops or spray.

For buccal administration, the compositions may take the form of tablets or lozenges formulated in a conventional manner.

For administration by inhalation, the compounds for use according to the present invention are conveniently delivered in the form of a dry powder inhaler, or an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

Pharmaceutical compositions of the present invention can be manufactured in a manner that is itself known, e.g., by means of conventional mixing, dissolving, granulating, dragee-making, levigating, emulsifying, encapsulating, entrapping or lyophilizing processes.

In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, lyophilized solid or paste, semi-solid, or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

The following pharmaceutical formulations 1 and 2 are illustrative only and are not intended to limit the scope of the invention in any way. "Active Ingredient", refers to a compound according to Structural Formula I or salts thereof.

Formulation 1

Hard gelatin capsules are prepared using the following ingredients:

|  | Quantity (mg/capsule) |
|---|---|
| Active Ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

In yet another embodiment of the compounds of the present invention, the compound is radiolabelled, such as with carbon-14, or tritiated. Said radiolabelled or tritiated compounds are useful as reference standards for in vitro assays to identify new PPARα and or PPARδ agonists.

SYNTHESIS

Compounds of the present invention have been formed as specifically described in the examples. Further, many compounds are prepared as more generally as shown in the following schematic. Alternative synthesis methods may also be effective and are known to the skilled artisan.

Scheme 1

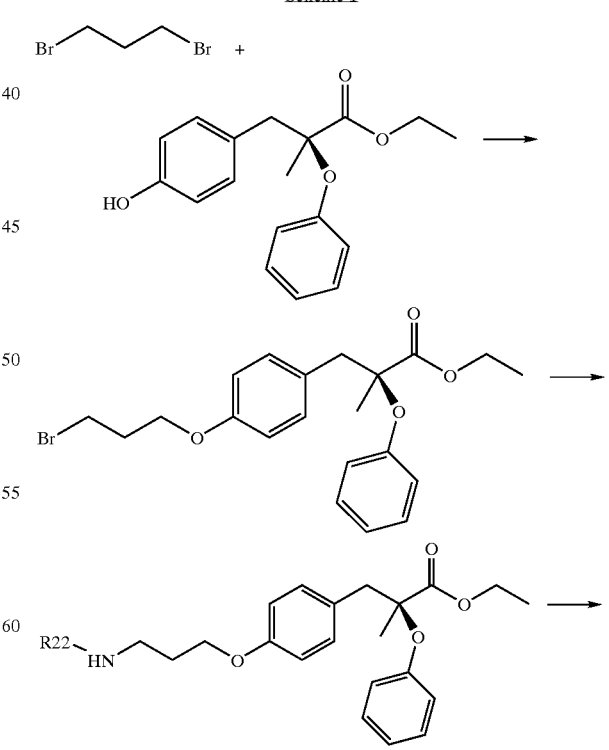

*R22NH$_2$ = BnNH$_2$, CH$_3$NH$_2$, n-propyl amine, aniline

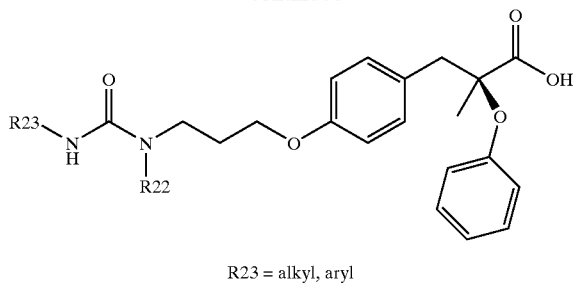

R23 = alkyl, aryl

General Experimental Procedure for the synthesis of urea products.

Step 1.

3-[4-(3-Bromo-propoxy)phenyl]-2-methyl-2-phenoxypropionic acid ethyl ester

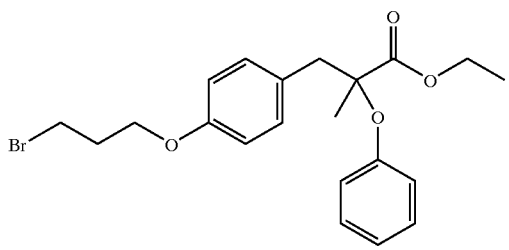

3-(4-Hydroxyphenyl)-2-methyl-2-phenoxypropionic acid ethyl ester (4.0 g, 13.3 mmol) and 1,3-dibromopropane (7.0 mL, 66.6 mmol) are dissolved in methyl ethyl ketone (100 mL). Powdered $K_2CO_3$ (2.4 g, 17.3 mmol) is added. The mixture is heated under reflux for 4 h, cooled, filtered and concentrated to an oil. The crude oil is chromatographed (silica gel; hexane/EtOAc, 5:1 to 1:4) to afford the title compound (5.0 g, 89%). MS (ESI) m/z 421 (M+H)$^+$.

Step 2.

2-Methyl-3-[4-(3-alkylamino-propoxy)phenyl]2-phenoxypropionic acid ethyl ester

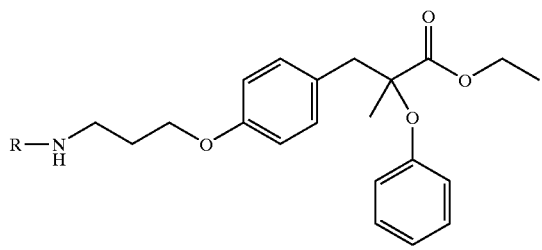

To a solution of the appropriate amine (8.5 mmol) in ethanol (10 mL) is added 3-[4-(3-bromo-propoxy)phenyl]-2-methyl-2-phenoxypropionic acid ethyl ester (0.72 g, 1.7 mmol). The mixture is stirred at room temperature for 4 h. Washed with water, extracted with EtOAc, the organic layer is dried (MgSO$_4$), concentrated and chromatographed (silica gel; EtOAc/MeOH, 10:0 to 10:1). The products are isolated as oils, yields 30–50%.

Step 3.

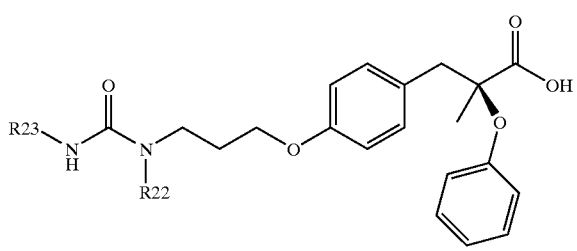

R22 and R23 are as defined above in Scheme I.

3-{4-[3-(3-Substituted-1-alkyl-ureido)-propoxy]phenyl}-2-methyl-2phenoxypropionic acid To a solution of the appropriate 2-methyl-3-[4-(3-alkyl or 3-aryl amino-propoxy)phenyl]-2-phenoxypropionic acid ethyl ester (50 mg, 0.13 mmol) in $CH_2Cl_2$ (2 mL) is added the corresponding isocyante (0.20 mmol). The mixture is allowed to stand for 3 h at room temperature. The solvent is evaporated and the residue is treated with 5.0 N NaOH in methanol at 60° C. for 2 h. After cooling, the reaction is acidified with 1N HCl, extracted with EtOAc and concentrated. The residue is purified by LC/MS to give pure acid.

Scheme 2

3-{4-[3-(3-Substituted-ureido)-propoxy]phenyl}-2-methyl-2-phenoxypropionic acid

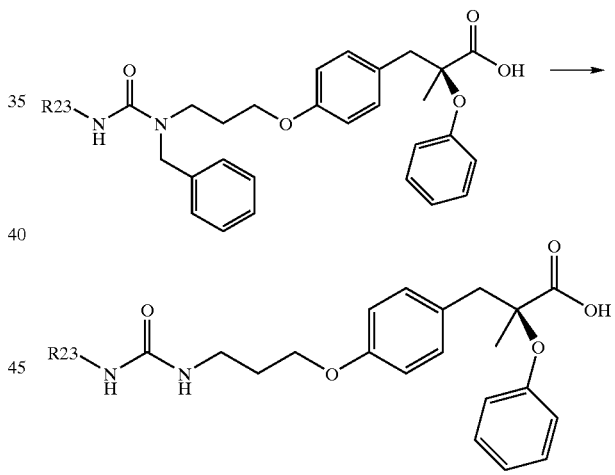

The desired 3-{4-[3-(3-Substituted-1-benzyl-ureido)-propoxy]phenyl}-2-methyl-2phenoxypropionic acid (15 mg) is dissolved in EtOAc/HOAc (1:1). It is hydrogenated in the presence of Pd—C (10%, 5 mg) at room temperature for 16 h. Solvent is evaporated. The title compound is obtained.

The Examples provided herein are illustrative of the invention claimed herein and are not intended to limit the scope of the claimed invention in any way.

EXEMPLIFICATION

Instrumental Analysis

Infrared spectra are recorded on a Perkin Elmer 781 spectrometer. $^1$H NMR spectra are recorded on a Varian 400 MHz spectrometer at ambient temperature. Data are reported as follows: chemical shift in ppm from internal standard tetramethylsilane on the δ scale, multiplicity (b=broad, s=singlet, d=doublet, t=triplet, q=quartet, qn=quintet and m=multiplet), integration, coupling constant (Hz) and assignment. $^{13}$C NMR are recorded on a Varian 400 MHz spectrometer at ambient temperature. Chemical shifts are reported in ppm from tetramethylsilane on the δ scale, with the solvent resonance employed as the internal standard (CDCl$_3$ at 77.0 ppm and DMSO-d$_6$ at 39.5 ppm). High resolution mass spectra are obtained on VG ZAB 3F or VG 70 SE spectrometers. Analytical thin layer chromatography is performed on EM Reagent 0.25 mm silica gel 60-F plates. Visualization is accomplished with UV light.

Exemplified Compounds

EXAMPLES prepared using the process described herein above.

| Example # | Structure | mol. Weight |
|---|---|---|
| 1 | 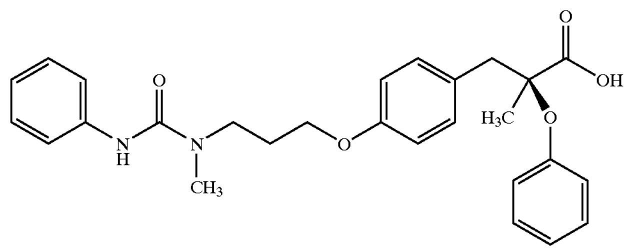 | 462.54 |
| 2 | 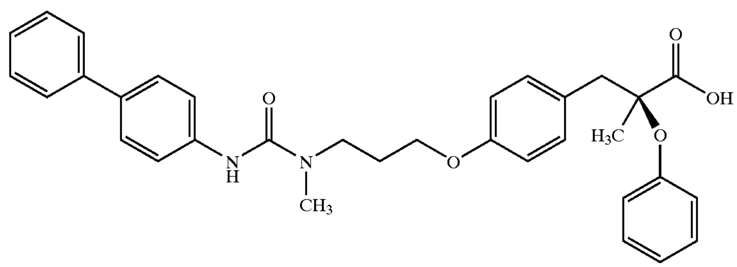 | 538.64 |
| 3 | 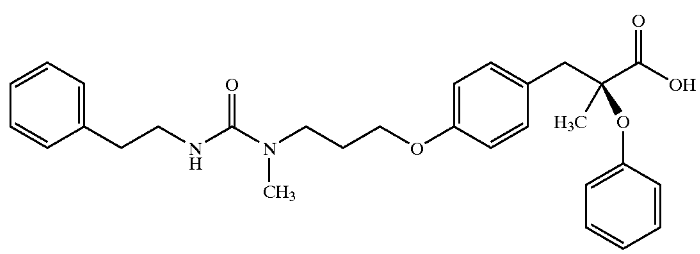 | 490.60 |
| 4 | 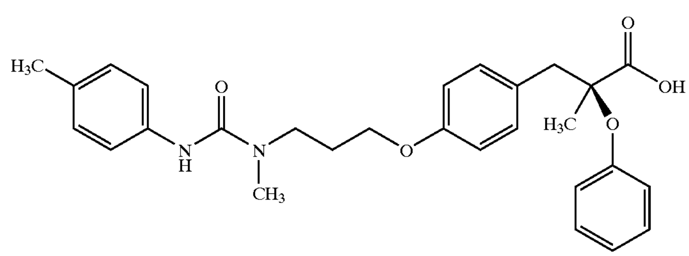 | 476.57 |
| 5 | 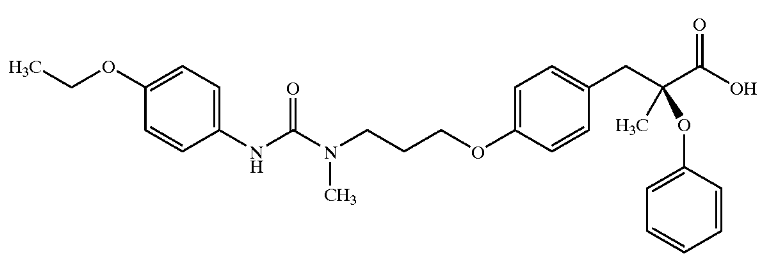 | 506.60 |

-continued

| Example # | Structure | mol. Weight |
|---|---|---|
| 6 | 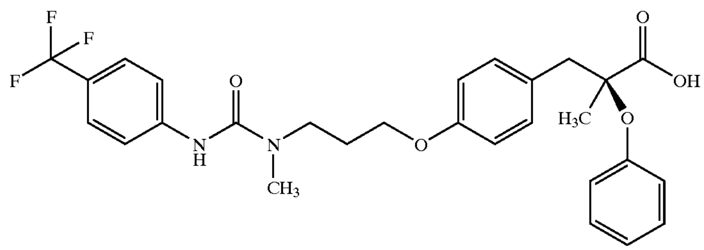 | 530.54 |
| 7 | 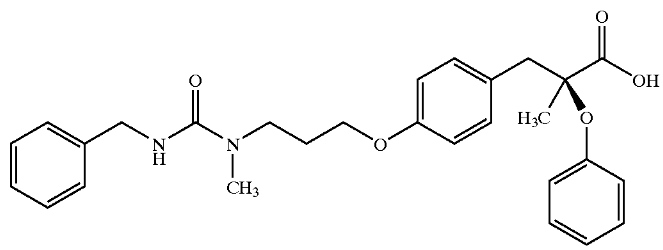 | 476.57 |
| 8 | 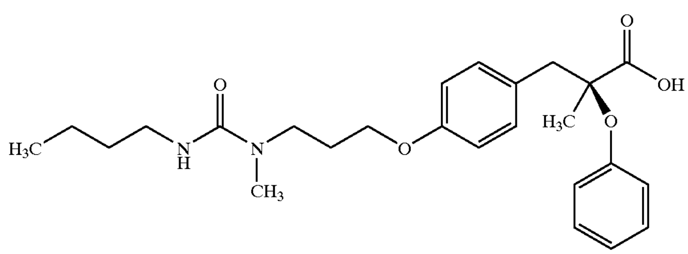 | 442.55 |
| 9 | Chiral | 504.62 |
| 10 | Chiral | 518.65 |

-continued

| Example # | Structure | mol. Weight |
|---|---|---|
| 11 | Chiral | 552.67 |
| 12 | Chiral | 566.69 |
| 13 | Chiral | 544.69 |
| 14 | Chiral | 538.64 |
| 15 | Chiral | 552.67 |

-continued

| Example # | Structure | mol. Weight |
|---|---|---|
| 16 | 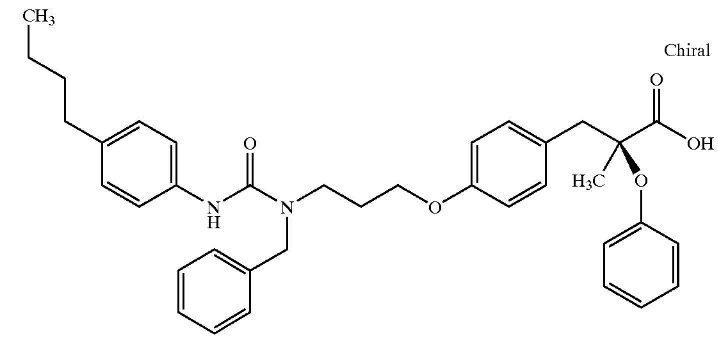 | 594.75 |
| 17 | 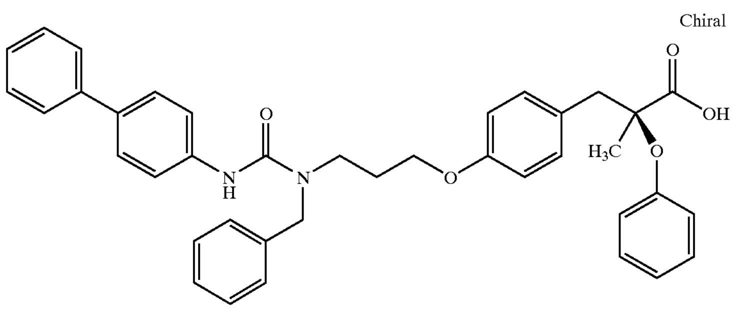 | 614.74 |
| 18 | 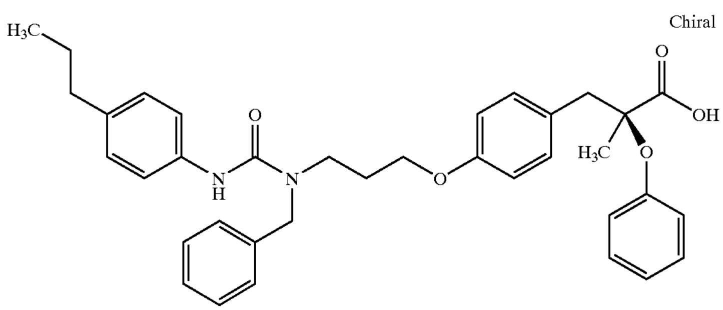 | 582.69 |
| 19 | 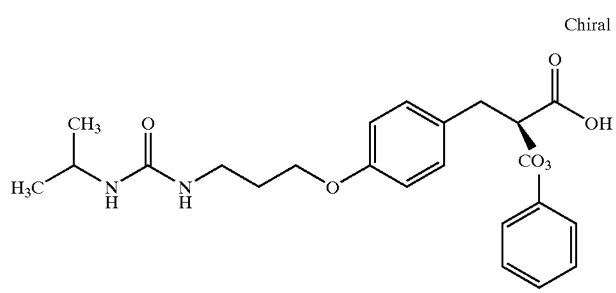 | 414.50 |
| 20 | 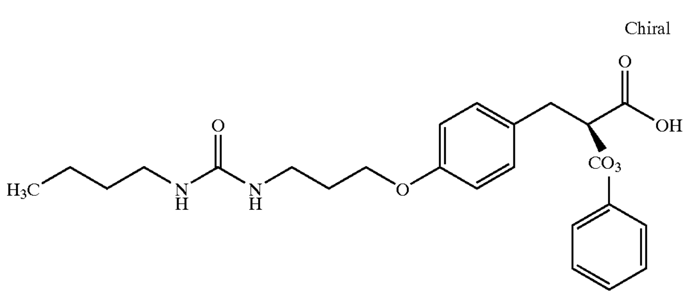 | 428.53 |

-continued

| Example # | Structure | mol. Weight |
|---|---|---|
| 21 | Chiral | 476.57 |
| 22 | Chiral | 454.56 |
| 23 | Chiral | 448.52 |
| 24 | Chiral | 462.54 |
| 25 | Chiral | 504.62 |

| Example # | Structure | mol. Weight |
|---|---|---|
| 26 | Chiral | 492.57 |
| 27 | Chiral | 636.72 |
| 28 | Chiral | 616.73 |
| 29 | 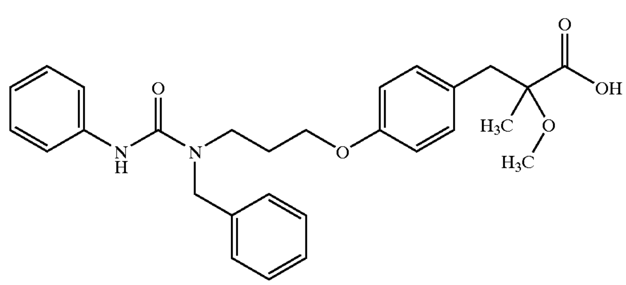 | 476.57 |
| 30 | 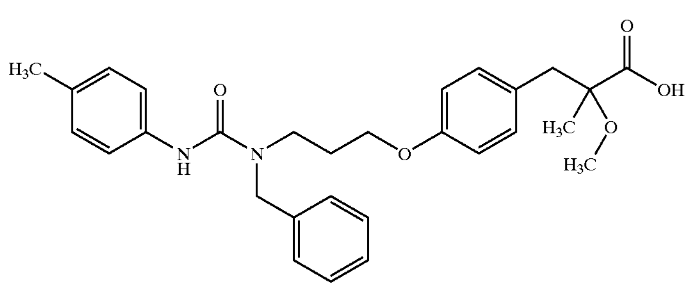 | 490.60 |

| Example # | Structure | mol. Weight |
|---|---|---|
| 31 | 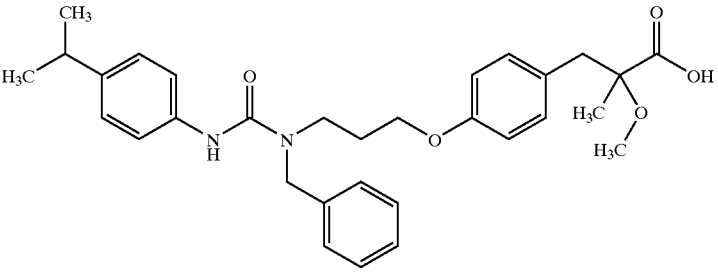 | 518.65 |
| 32 | 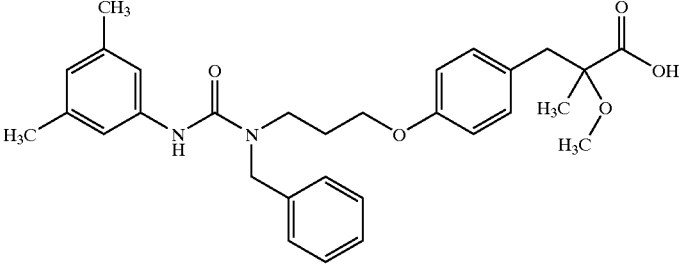 | 504.62 |
| 33 | 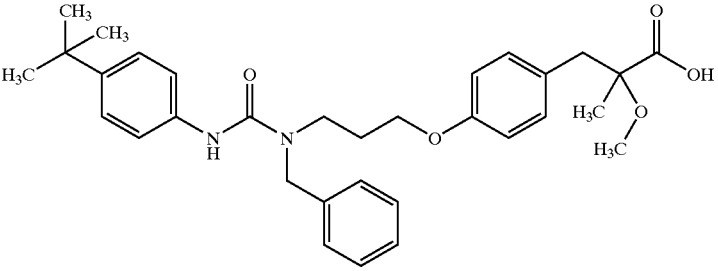 | 532.68 |
| 34 | 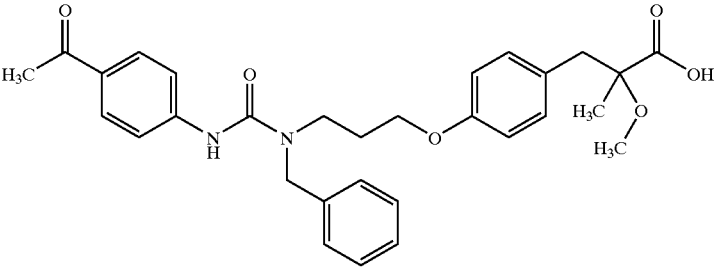 | 518.61 |
| 35 | 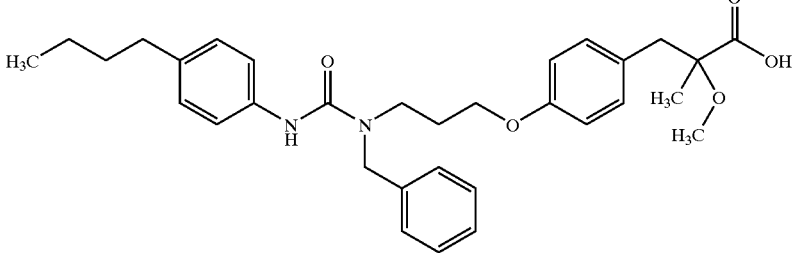 | 532.68 |

-continued

| Example # | Structure | mol. Weight |
|---|---|---|
| 36 | 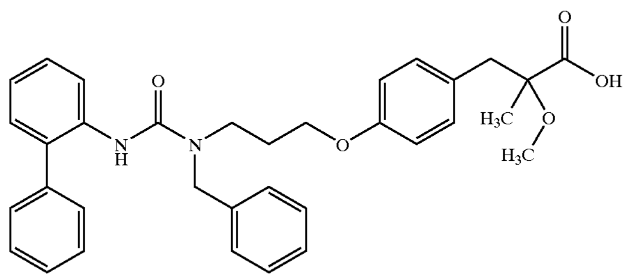 | 552.67 |
| 37 | 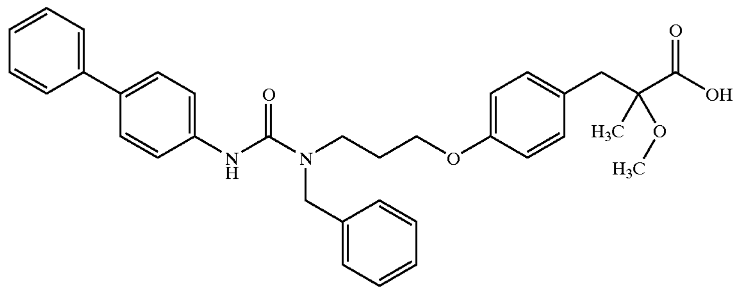 | 552.67 |
| 38 | 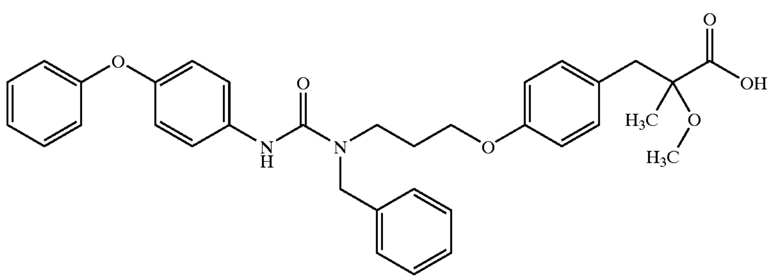 | 568.67 |
| 39 | Chiral | 456.58 |
| 40 | Chiral | 470.61 |

| Example # | Structure | mol. Weight |
|---|---|---|
| 41 | 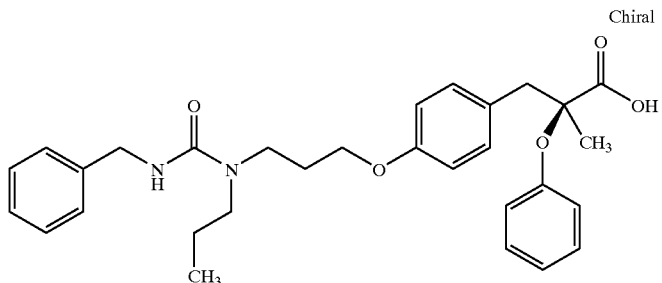 | 504.62 |
| 42 | 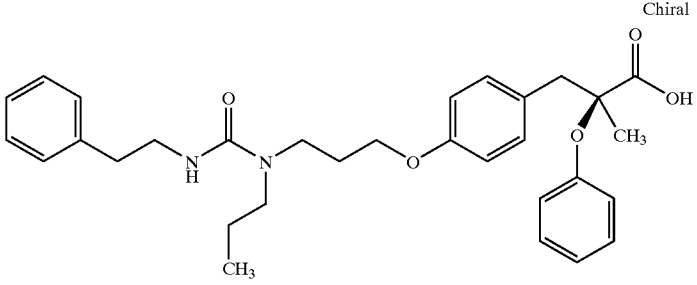 | 518.65 |
| 43 | 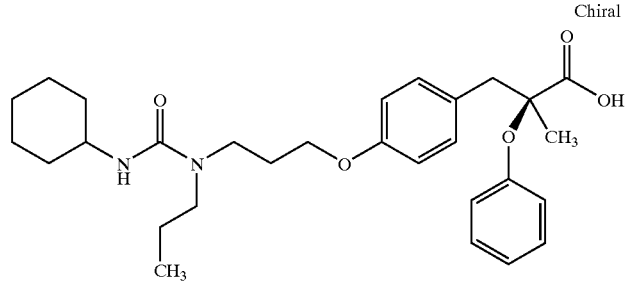 | 496.64 |
| 44 | 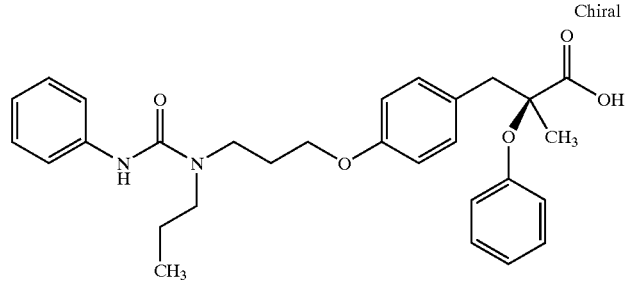 | 490.60 |
| 45 | 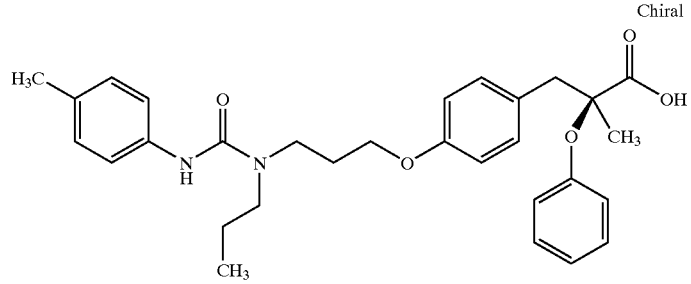 | 504.62 |

| Example # | Structure | mol. Weight |
|---|---|---|
| 46 | 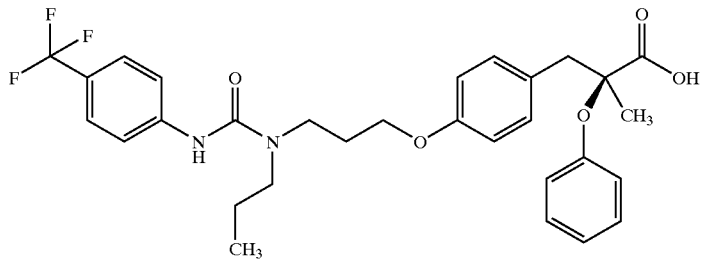 | 558.59 |
| 47 | 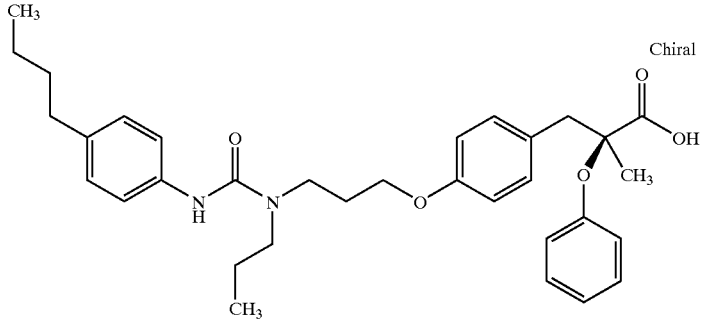 | 546.70 |
| 48 | 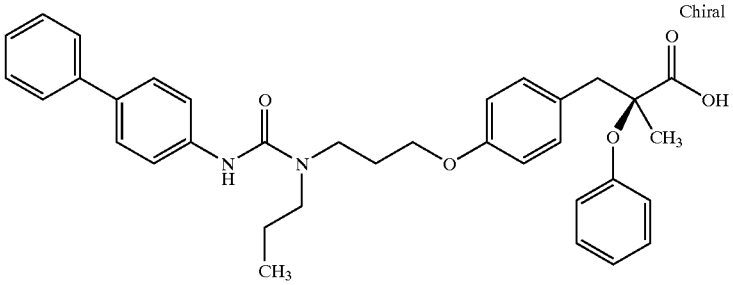 | 566.69 |
| 49 | 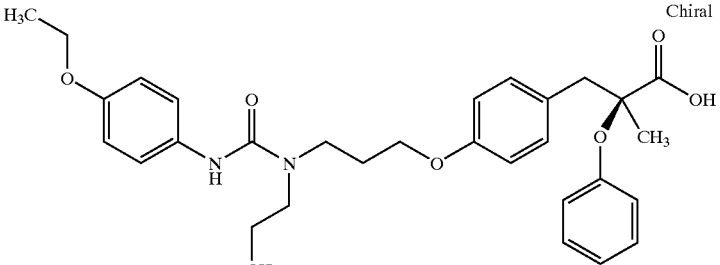 | 534.65 |
| 50 | 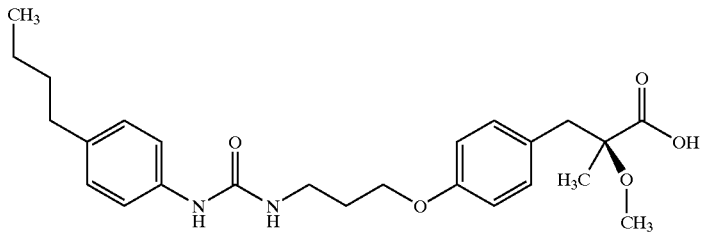 | 442.55 |

-continued

| Example # | Structure | mol. Weight |
|---|---|---|
| 51 | 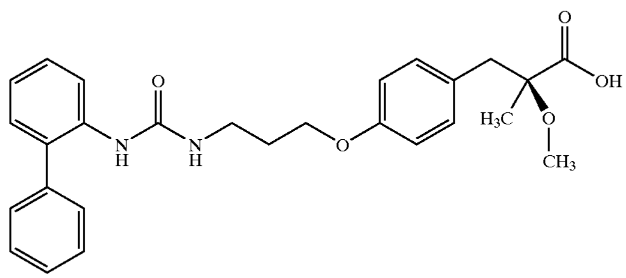 | 462.54 |
| 52 | 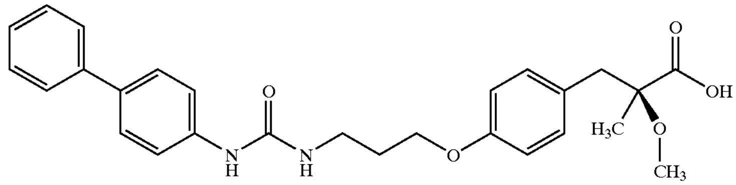 | 462.54 |
| 53 | 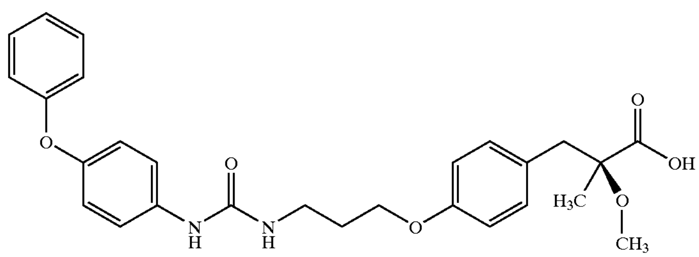 | 478.54 |
| 54 | Chiral | 582.69 |
| 55 | Chiral | 582.69 |

-continued

| Example # | Structure | mol. Weight |
|---|---|---|
| 56 | Chiral | 552.67 |
| 57 | Chiral | 538.64 |
| 58 | Chiral | 580.72 |
| 59 | Chiral | 574.67 |

| Example # | Structure | | mol. Weight |
|---|---|---|---|
| 60 | 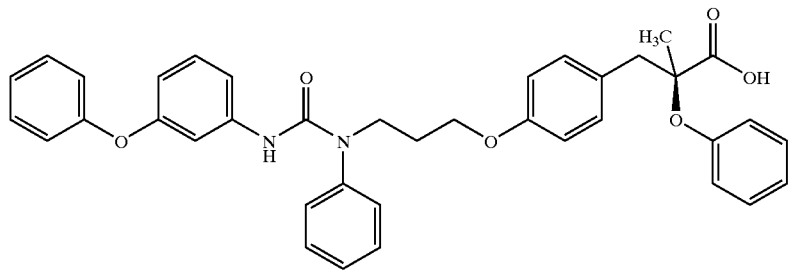 | Chiral | 616.71 |
| 61 | 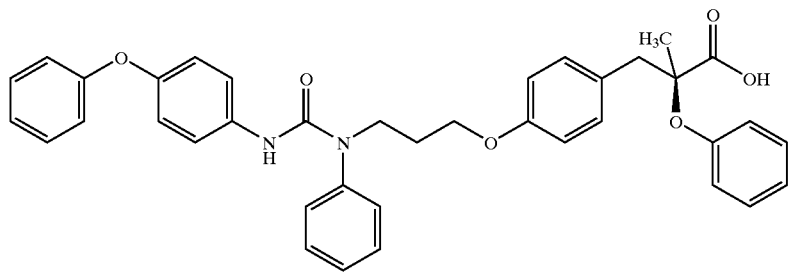 | Chiral | 616.71 |
| 62 | 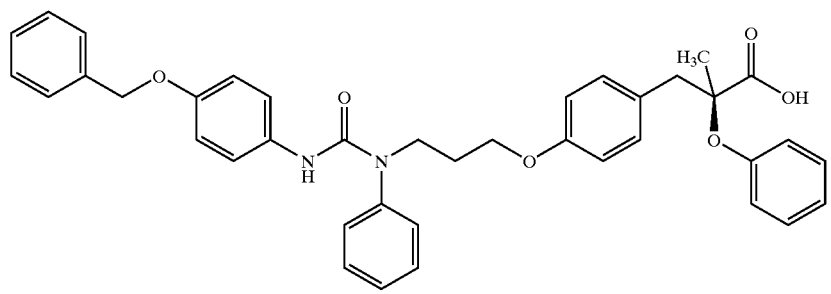 | Chiral | 630.74 |
| 63 | 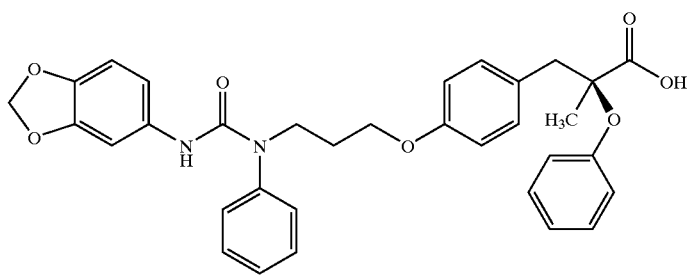 | Chiral | 568.62 |

-continued

| Example # | Structure | mol. Weight |
|---|---|---|
| 64 | Chiral | 564.68 |
| 65 | Chiral | 630.74 |
| 66 | Chiral | 630.74 |
| 67 | Chiral | 644.76 |

-continued

| Example # | Structure | mol. Weight |
|---|---|---|
| 68 | Chiral | 582.65 |

Biological Assays

Binding and Cotransfection Studies

The in vitro potency of compounds in modulating PPARγ and PPARα receptors are determined by the procedures detailed below. DNA-dependent binding (ABCD binding) is carried out using SPA technology with PPAR receptors. Tritium-labeled PPARα and PPARγ agonists are used as radioligands for generating displacement curves and $IC_{50}$ values with compounds of the invention. Cotransfection assays are carried out in CV-1 cells. The reporter plasmid contained an acylCoA oxidase (AOX) PPRE and TK promoter upstream of the luciferase reporter cDNA. Appropriate PPARs and RXRα are constitutively expressed using plasmids containing the CMV promoter. For PPARα and PPARβ, interference by endogenous PPARγ in CV-1 cells is an issue. In order to eliminate such interference, a GAL4 chimeric system is used in which the DNA binding domain of the transfected PPAR is replaced by that of GAL4, and the GAL4 response element is utilized in place of the AOX PPRE. Cotransfection efficacy is determined relative to PPARα agonist and PPARγ agonist reference molecules. Efficacies are determined by computer fit to a concentration-response curve, or in some cases at a single high concentration of agonist (10 μM). For binding or cotransfection studies with receptors other than PPARs, similar assays are carried out using appropriate ligands, receptors, reporter constructs, etc., for that particular receptor.

These studies are carried out to evaluate the ability of compounds of the invention to bind to and/or activate various nuclear transcription factors, particularly huPPARα ("hu" indicates "human") and huPPARγ. These studies provide in vitro data concerning efficacy and selectivity of compounds of the invention. Furthermore, binding and cotransfection data for compounds of the invention are compared with corresponding data for marketed compounds that act on either huPPARα or huPPARγ.

Binding and cotransfection data for representative compounds of the invention are compared with corresponding data for reference to determine the binding.

The binding and cotransfection efficacy values found, for compounds of this invention which are useful for modulating a PPAR alpha receptor, are ≦100 nM and ≧50%, respectively. When coagoanist modulators are desired, the values may be balanced against selectivity for the gamma or another desired PPAR receptor subtype.

Evaluation of Triglyceride Reduction and HDL Cholesterol Elevation in HuapoAI Transgenic Mice Studies are performed to evaluate the effect of compounds of the present invention upon HDL and triglyceride levels in human apoAI mice. For each compound tested, seven to eight week old male mice, transgenic for human apoAI (C57BL/6-tgn(apoal)lrub, Jackson Laboratory, Bar Harbor, Me.) are acclimated in individual cages for two weeks with standard chow diet (Purina 5001) and water provided ad libitum. After the acclimation, mice and chow are weighed and assigned to test groups (n=5) with randomization by body weight. Mice are dosed daily by oral gavage for 8 days using a 29 gauge, 1½ inch curved feeding needle (Popper & Sons). The vehicle for the controls, test compounds and the positive control (fenofibrate 100 mg/kg) is 1% carboxymethylcellulose (w/v) with 0.25% tween 80 (w/v). All mice are dosed daily between 6 and 8 a.m. with a dosing volume of 0.2 ml. Prior to termination, animals and diets are weighed and body weight change and food consumption are calculated. Three hours after last dose, mice are euthanized with CO2 and blood is removed (0.5–1.0 ml) by cardiac puncture. After sacrifice, the liver, heart, and epididymal fat pad are excised and weighed. Blood is permitted to clot and serum is separated from the blood by is centrifugation.

Cholesterol and triglycerides are measured calorimetrically using commercially prepared reagents (for example, as available from Sigma #339–1000 and Roche #450061 for triglycerides and cholesterol, respectively). The procedures are modified from published work (McGowan M. W. et al., Clin Chem 29:538–542,1983; Allain C. C. et al., Clin Chem 20:470–475,1974. Commercially available standards for triglycerides and total cholesterol, respectively, commercial quality control plasma, and samples are measured in duplicate using 200 μl of reagent. An additional aliquot of sample, added to a well containing 200 μl water, provided a blank for each specimen. Plates are incubated at room temperature on a plate shaker and absorbance is read at 500 nm and 540 nm for total cholesterol and triglycerides, respectively. Values for the positive control are always within the expected range and the coefficient of variation for samples is below 10%. All samples from an experiment are assayed at the same time to minimize inter-assay variability.

Serum lipoproteins are separated and cholesterol quantitated by fast protein liquid chromatography (FPLC) coupled to an in line detection system. Samples are applied to a Superose 6 HR size exclusion column (Amersham Pharmacia Biotech) and eluted with phosphate buffered saline-EDTA at 0.5 ml/min. Cholesterol reagent (Roche Diagnostics Chol/HP 704036) at 0.16 ml/min mixed with the column effluent through a T-connection and the mixture passed through a 15 m×0.5 mm id knitted tubing reactor immersed in a 37 C water bath. The colored product produced in the presence of cholesterol is monitored in the flow strem at 505 nm and the analog voltage from the monitor is converted to a digital signal for collection and analysis. The change in voltage corresponding to change in cholesterol concentration is plotted vs time and the area under the curve corresponding to the elution of very low density lipoprotein (VLDL), low density lipoprotein (LDL) and high density lipoprotein (HDL) is calculated using Perkin Elmer Turbochrome software. Valued for triglyceride levels in the control mice and for HDL cholesterol levels in fenofibrate-treated mice are considered in the selection of especially desired compounds of this invention.

Triglyceride Serum Levels in Mice Dosed with a Compound of the Invention is Compared to Mice Receiving the Vehicle to identify compounds which could be particularly useful for lowering triglycerides. Generally, triglyceride decreases of greater than or equal to 30% (thirty percent) compared to control following a 30 mg/kg dose suggests a compound that can be especially useful for lowering triglyceride levels.

The percent increase of HDLc serum levels in mice receiving a compound of the invention is compared to mice receiving vehicle to identify compounds of the invention that could be particularly useful for elevating HDL levels. Generally, and increase of greater than or equal to 25% (twenty five percent) increase in HDLc level following a 30 mg/kg dose suggests a compound that can be especially useful for elevating HDLc levels.

It may be particularly desirable to select compounds of this invention that both lower triglyceride levels and increase HDLc levels. However, compounds that either lower triglyceride levels or increase HDLc levels may be desirable as well.

Evaluation of Glucose Levels in db/db Mice

The effects, upon plasma glucose of administering various dose levels of different compounds of the present invention and the PPAR gamma agonist rosiglitazone (BRL49653) or the PPAR alpha agonist fenofibrate, and the control, to male db/db mice, are studied.

Five week old male diabetic (db/db) mice [for example, C57BlKs/j-m+/+ Lepr(db), Jackson Laboratory, Bar Harbor, Me.] or lean littermates are housed 6 per cage with food and water available at all times. After an acclimation period of 2 weeks, animals are individually identified by ear notches, weighed, and bled via the tail vein for determination of initial glucose levels. Blood is collected (100 $\mu$l) from unfasted animals by wrapping each mouse in a towel, cutting the tip of the tail with a scalpel, and milking blood from the tail into a heparinized capillary tube. Sample is discharged into a heparinized microtainer with gel separator and retained on ice. Plasma is obtained after centrifugation at 4° C. and glucose measured immediately. Remaining plasma is frozen until the completion of the experiment, when glucose and triglycerides are assayed in all samples. Animals are grouped based on initial glucose levels and body weights. Beginning the following morning, mice are dosed daily by oral gavage for 7 days. Treatments are test compounds (30 mg/kg), a positive control agent (30 mg/kg) or vehicle [1% carboxymethylcellulose (w/v)/0.25% Tween80 (w/v); 0.3 ml/mouse]. On day 7, mice are weighed and bled (tail vein) 3 hours after dosing. Twenty-four hours after the $7^{th}$ dose (i.e., day 8), animals are bled again (tail vein). Samples obtained from conscious animals on days 0, 7 and 8 are assayed for glucose. After the 24 hour bleed, animals are weighed and dosed for the final time. Three hours after dosing on day 8, animals are anesthetized by inhalation of isoflurane and blood obtained via cardiac puncture (0.5–0.7 ml). Whole blood is transferred to serum separator tubes, chilled on ice and permitted to clot. Serum is obtained after centrifugation at 4° C. and frozen until analysis for compound levels. After sacrifice by cervical dislocation, the liver, heart and epididymal fat pads are excised and weighed.

Glucose is measured calorimetrically using commercially purchased reagents. According to the manufacturers, the procedures are modified from published work (McGowan, M. W., Artiss, J. D., Strandbergh, D. R. & Zak, B. Clin Chem, 20:470–5 (1974) and Keston, A. Specific calorimetric enzymatic analytical reagents for glucose. Abstract of papers 129th Meeting ACS, 31C (1956).); and depend on the release of a mole of hydrogen peroxide for each mole of analyte, coupled with a color reaction first described by Trinder (Trinder, P. Determination of glucose in blood using glucose oxidase with an alternative oxygen acceptor. Ann Clin Biochem, 6:24 (1969)). The absorbance of the dye produced is linearly related to the analyte in the sample. The assays are further modified in our laboratory for use in a 96 well format. The commercially available standard for glucose, commercially available quality control plasma, and samples (2 or 5 $\mu$l/well) are measured in duplicate using 200 $\mu$l of reagent. An additional aliquot of sample, pipetted to a third well and diluted in 200 $\mu$l water, provided a blank for each specimen. Plates are incubated at room temperature for 18 minutes for glucose on a plate shaker (DPC Micormix 5) and absorbance read at 500 nm on a plate reader. Sample absorbances are compared to a standard curve (100–800 for glucose). Values for the quality control sample are always within the expected range and the coefficient of variation for samples is below 10%. All samples from an experiment are assayed at the same time to minimize inter-assay variability.

Compounds of the present invention that significantly reduced db/db mouse plasma glucose levels while resulting in body weight gains that are less than those observed for rosiglitazone are especially desirable.

Evaluation of the Effects of Compounds of the Present Invention upon $A^y$ Mice Body Weight, Fat Mass, Glucose and Insulin Levels Female $A^y$ Mice Female $A^y$ mice are singly housed, maintained under standardized conditions (22° C., 12 h light:dark cycle), and provided free access to food and water throughout the duration of the study. At twenty weeks of age the mice are randomly assigned to vehicle control and treated groups based on body weight and body fat content as assessed by DEXA scanning (N=6). Mice are then dosed via oral gavage with either vehicle or a Compound of this invention (50 mg/kg) one hour after the initiation of the light cycle (for example, about 7 A.M.) for 18 days. Body weights are measured daily throughout the study. On day 14 mice are maintained in individual metabolic chambers for indirect calorimetry assessment of energy expenditure and fuel utilization. On day 18 mice are again subjected to DEXA scanning for post treatment measurement of body composition.

The results of p.o. dosing of compound for 18 days on body weight, fat mass, and lean mass are evaluated and suggest which compounds of this invention can be especially useful for maintaining desirable weight and/or promoting desired lean to fat mass.

Indirect calorimetry measurements reveal a significant reduction in respiratory quotient (RQ) in treated animals during the dark cycle [0.864±0.013 (Control) vs.

0.803±0.007 (Treated); p<0.001] for animals treated with especially desirable compounds of this invention. This reduction in RQ is indicative of an increased utilization of fat during the animals' active (dark) cycle. Additionally, treated animals displaying significantly higher rates of energy expenditure than control animals (17.40±0.49 vs. 13.62±0.26 kcal/kg/hr, respectively) can indentify especially desirable compounds of this invention.

Male KK/A$^y$ Mice

Male KK/A$^y$ mice are singly housed, maintained under standardized conditions (22° C., 12 h light:dark cycle), and provided free access to food and water throughout the duration of the study. At twenty-two weeks of age the mice are randomly assigned to vehicle control and treated groups based on plasma glucose levels. Mice are then dosed via oral gavage with either vehicle or a Compound of this invention (30 mg/kg) one hour after the initiation of the light cycle (7 A.M.) for 14 days. Plasma glucose, triglyceride, and insulin levels are assessed on day 14.

The results of p.o. dosing of compound for 14 days on plasma glucose, triglycerides, and insulin are evaluated to identify compounds of this invention that can be especially desired.

Method to Elucidate the LDL-cholesterol Total-cholesterol and Triglyceride Lowering Effect Male Syrian hamsters (Harlan Sprague Dawley) weighing 80–120 g are placed on a high-fat cholesterol-rich diet for two to three weeks prior to use. Feed and water are provided ad libitum throughout the course of the experiment. Under these conditions, hamsters became hypercholesterolemic showing plasma cholesterol levels between 180–280 mg/dl. (Hamsters fed with normal chow had a total plasma cholesterol level between 100–150 mg/dl.) Hamsters with high plasma cholesterol (180 mg/dl and above) are randomized into treatment groups based on their total cholesterol level using the GroupOptimizeV211.xls program.

A Compound of this invention is dissolved in an aqueous vehicle (containing CMC with Tween 80) such that each hamster received once a day approx. 1 ml of the solution by garvage at doses 3 and 30 mg/kg body weight. Fenofibrate (Sigma Chemical, prepared as a suspension in the same vehicle) is given as a known alpha-agonist control at a dose of 200 mg/kg, and the blank control is vehicle alone. Dosing is performed daily in the early morning for 14 days.

Quantification of Plasma Lipids:

On the last day of the test, hamsters are bled (400 ul) from the suborbital sinus while under isoflurane anesthesia 2 h after dosing. Blood samples are collected into heparinized microfuge tubes chilled in ice bath. Plasma samples are separated from the blood cells by brief centrifugation. Total cholesterol and triglycerides are determined by means of enzymatic assays carried out automatically in the Monarch equipment (Instrumentation Laboratory) following the manufacturer's precedure. Plasma lipoproteins (VLDL, LDL and HDL) are resolved by injecting 25 ul of the pooled plasma samples into an FPLC system eluted with phosphate buffered saline at 0.5 ml/min through a Superose 6 HR 10/30 column (Pharmacia) maintained room temp. Detection and characterization of the isolated plasma lipids are accomplished by postcolumn incubation of the effluent with a Cholesterol/HP reagent (for example, Roche Lab System; infused at 0.12 ml/min) in a knitted reaction coil maintained at 37° C. The intensity of the color formed is proportional to the cholesterol concentration and is measured photometrically at 505 nm.

The effect of administration of a Compound of this invention for 14 days is studied for the percent reduction in LDL level with reference to the vehicle group. The LDL-lowering efficacy for certain compounds of this invention is markedly more potent than that of fenofibrate. Compounds of this invention that decrease LDL greater than or equal to 30% (thirty percent) compared to vehicle can be especially desired.

The total-cholesterol and triglyceride lowering effects of a Compound of this invention is also studied. The data for reduction in total cholesterol and triglyceride levels after treatment with a compound of this invention for 14 days is compared to the vehicle to suggest compounds that can be particularly desired. The known control fenofibrate did not show significant efficacy under the same experimental conditions.

Method to Elucidate the Fibrinogen-Lowering Effect of PPAR Modulators

Zucker Fatty Rat Model:

The life phase of the study on fibrinogen-lowering effect of compounds of this invention is part of the life phase procedures for the antidiabetic studies of the same compounds. On the last (14$^{th}$) day of the treatment period, with the animals placed under surgical anesthesia, ~3 ml of blood is collected, by cardiac puncture, into a syringe containing citrate buffer. The blood sample is chilled and centrifuged at 4° C. to isolate the plasma that is stored at −70° C. prior to fibrinogen assay.

Quantification of Rat Plasma Fibrinogen:

Rat plasma fibrinogen levels are quantified by using a commercial assay system consists of a coagulation instrument following the manufacturer's protocol. In essence, 100 ul of plasma is sampled from each specimen and a 1/20 dilution is prepared with buffer. The diluted plasma is incubated at 37° C. for 240 seconds. Fifty microliters of clotting reagent thrombin solution (provided by the instrument's manufacturer in a standard concentration) is then added. The instrument monitors the clotting time, a function of fibrinogen concentration quantified with reference to standard samples. Compounds of this invention that lower fibrinogen level greater than vehicle can be especially desired.

Cholesterol and triglyceride lowering effects of compounds of this invention are also studied in Zucker rats.

Method to Elucidate the Anti-body Weight Gain and Anti-appetite Effects of Compounds of this Invention Fourteen-Day Study in Zucker Fatty Rat[1] or ZDF Rat[2] Models:

Male Zucker Fatty rats, non-diabetic (Charles River Laboratories, Wilmington, Mass.) or male ZDF rats (Genetic Models, Inc, Indianapolis, Ind.) of comparable age and weight are acclimated for 1 week prior to treatment. Rats are on normal chow and water is provided ad libitum throughout the course of the experiment.

Compounds of this invention to be studied are dissolved in an aqueous vehicle such that each rat receives once a day approximately 1 ml of the solution by garvage at doses 0.1, 0.3, 1 and 3 mg/kg body weight. Fenofibrate (Sigma Chemical, prepared as a suspension in the same vehicle) a known alpha-agonist given at doses of 300 mg/kg, as well as the vehicle are controls. Dosing is performed daily in the early morning for 14 days. Over the course of the experiment, body weight and food consumption are monitored. Using this assay, compounds of this invention that can result in significant weight reduction are identified.

Equivalents:

While this invention has been particularly shown and described with references to preferred embodiments thereof, it will be understood by those skilled in the art that various changes in form and details may be made therein without departing from the scope of the invention encompassed by the appended claims.

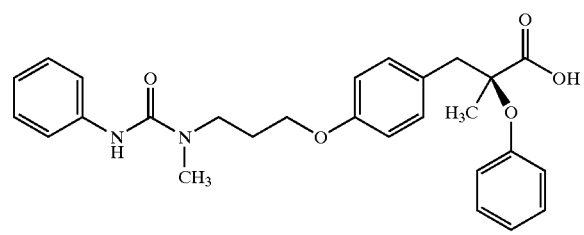

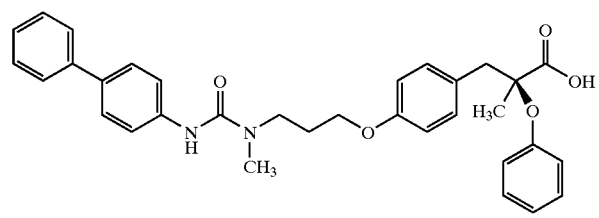

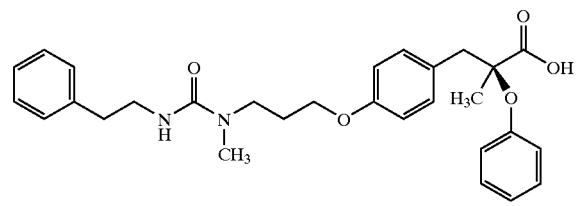

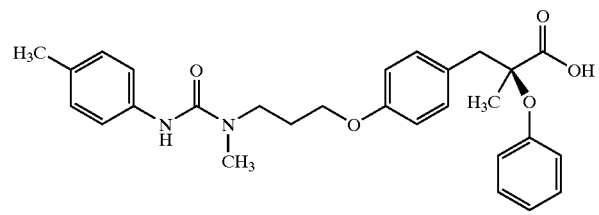

-continued
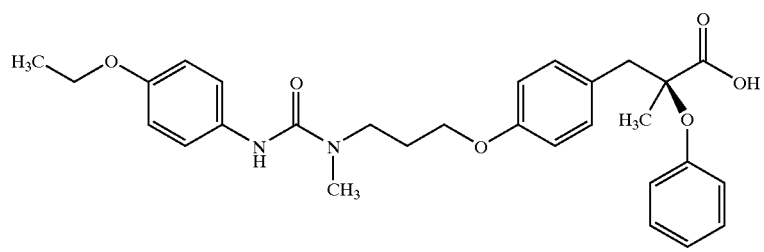
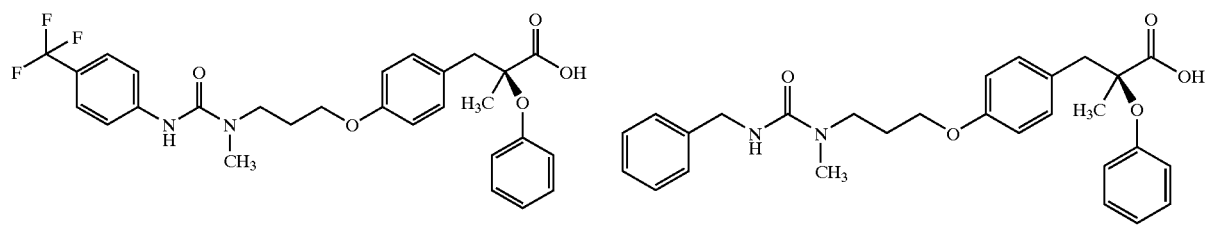
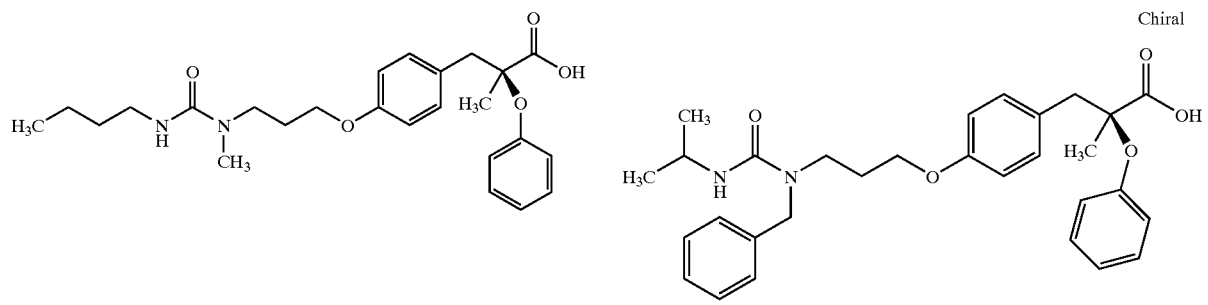
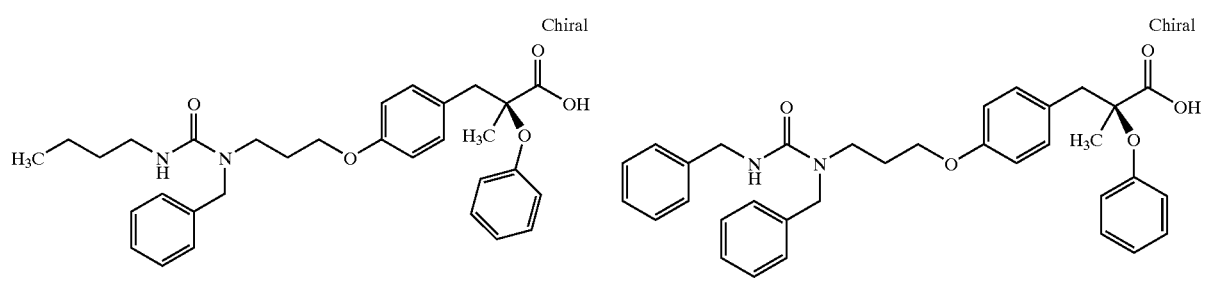
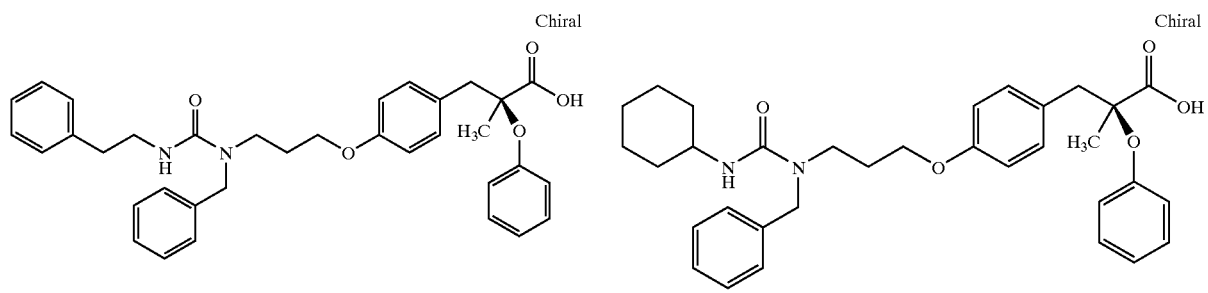
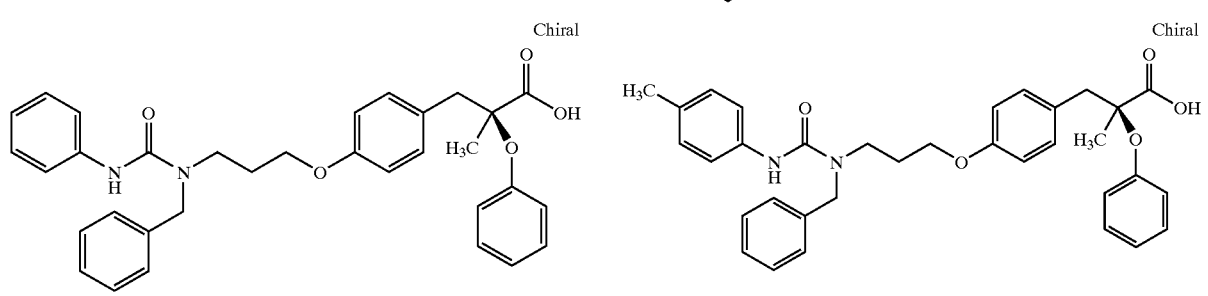

-continued
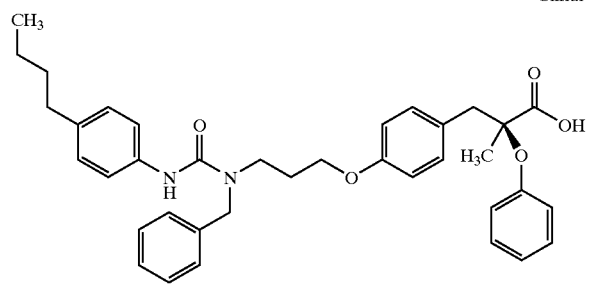
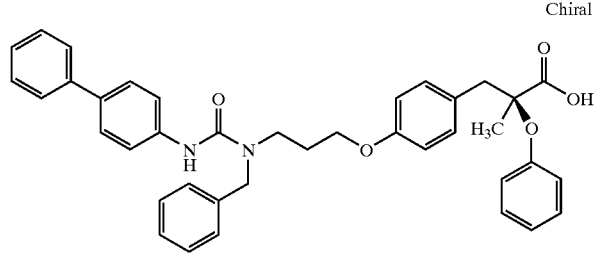
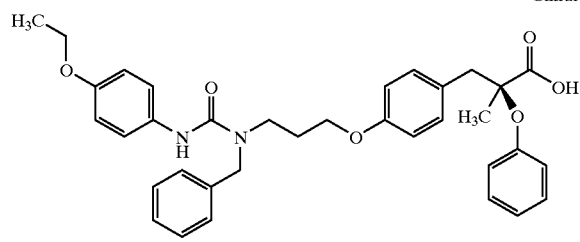
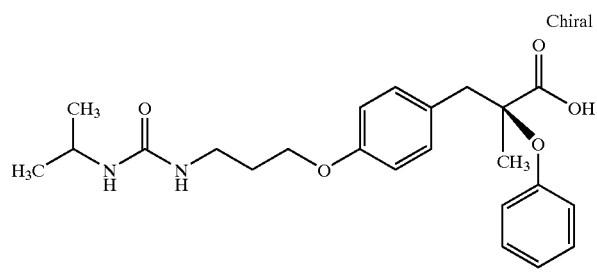
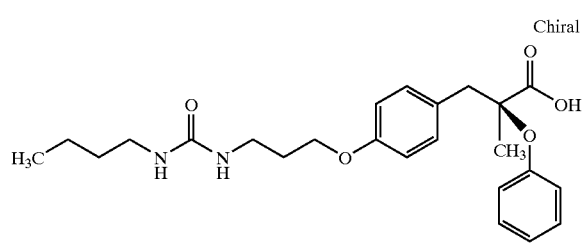
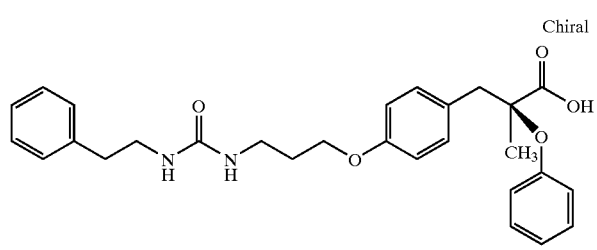
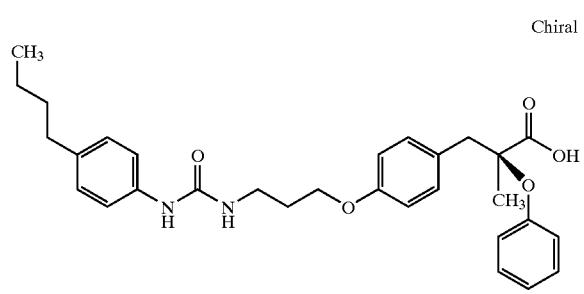
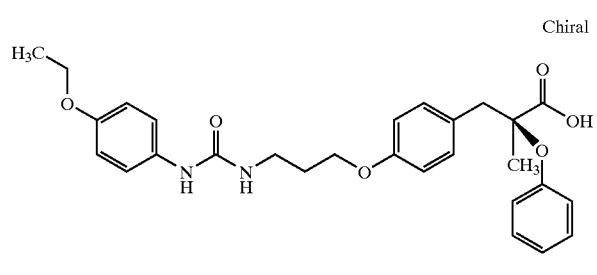
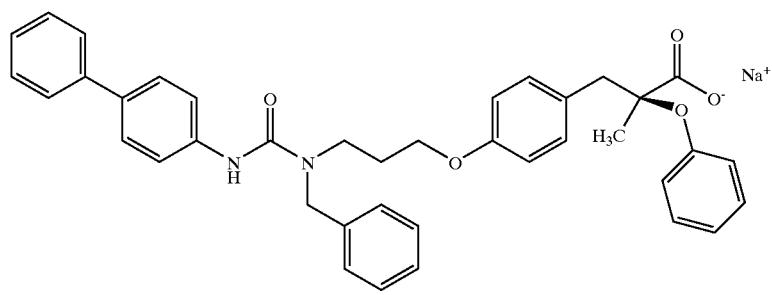

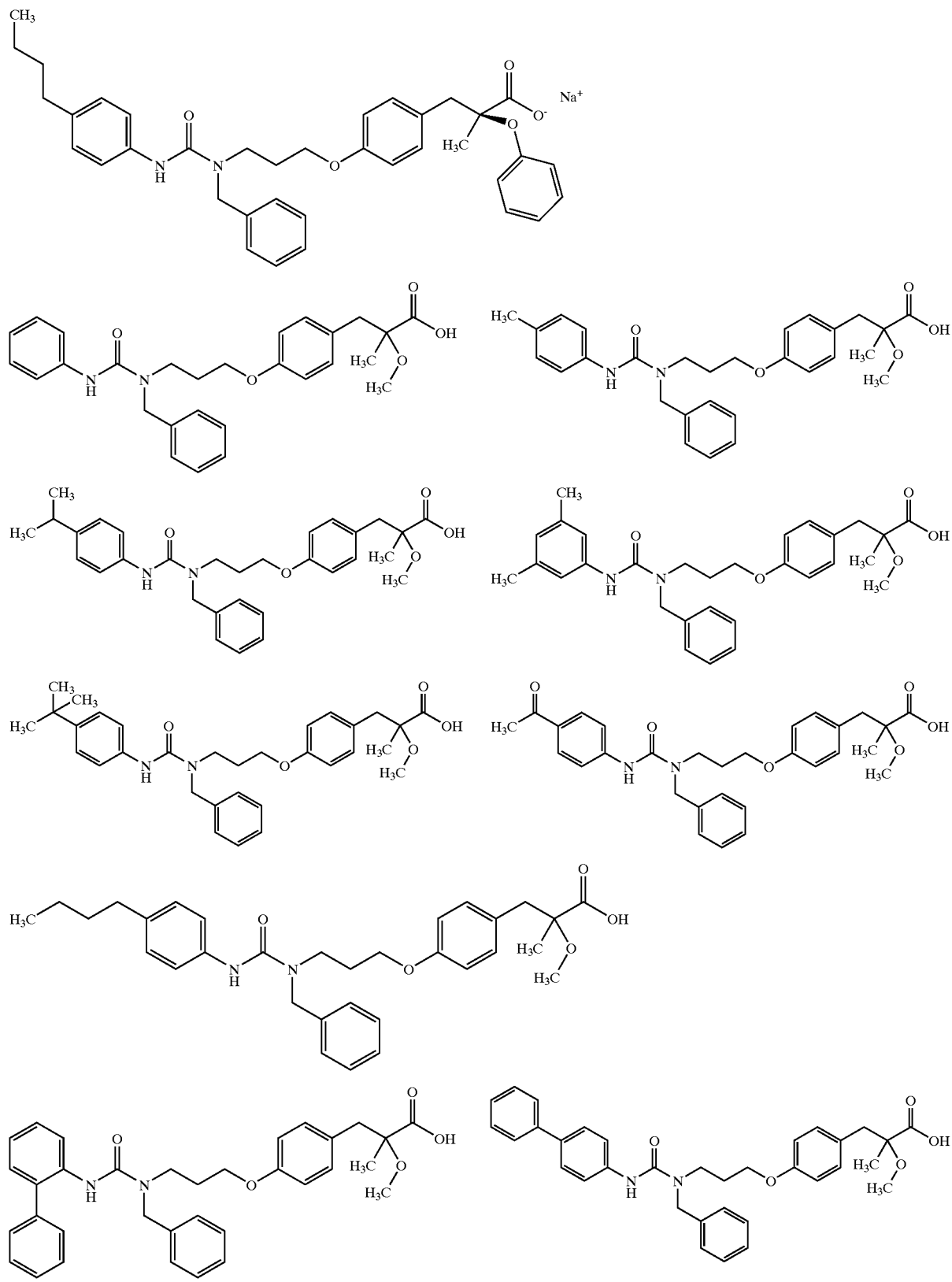

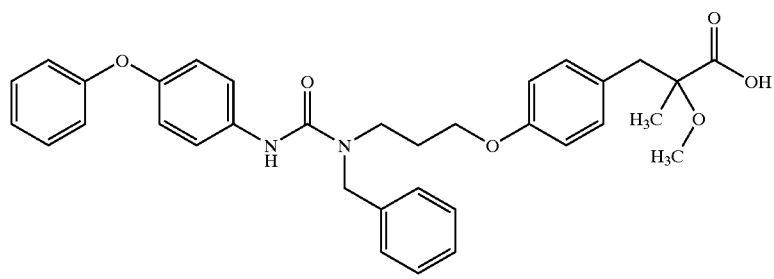
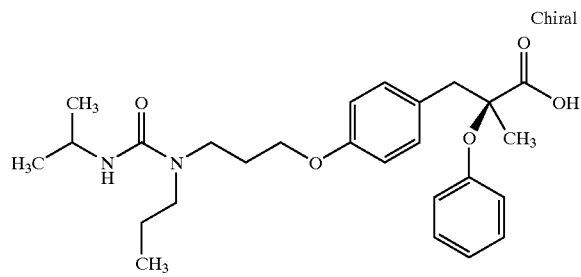
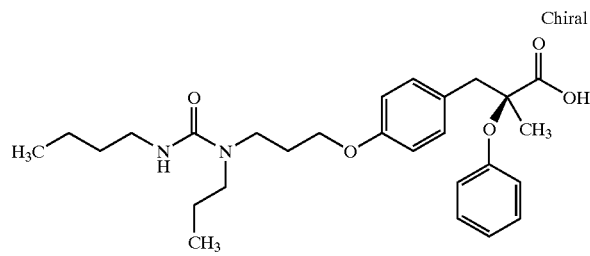
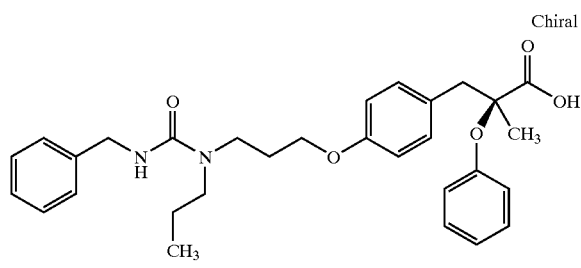
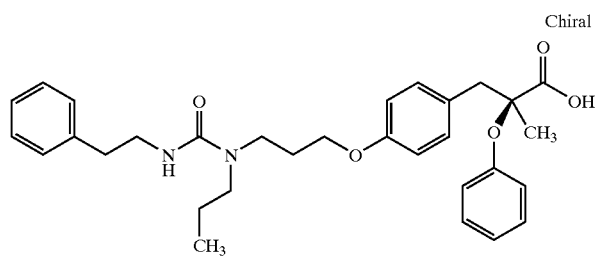
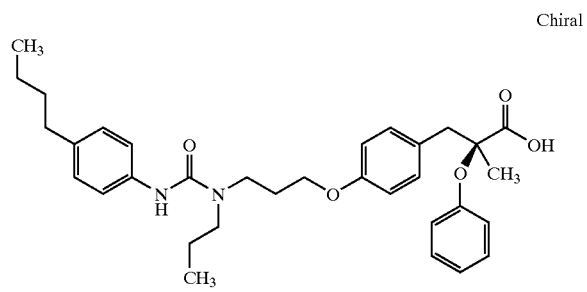
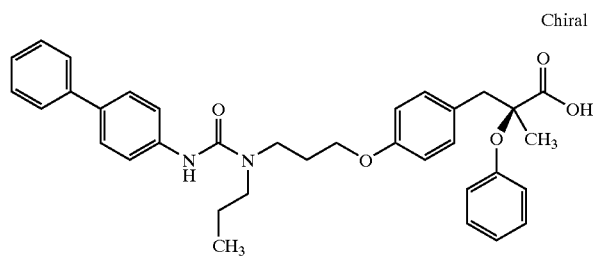
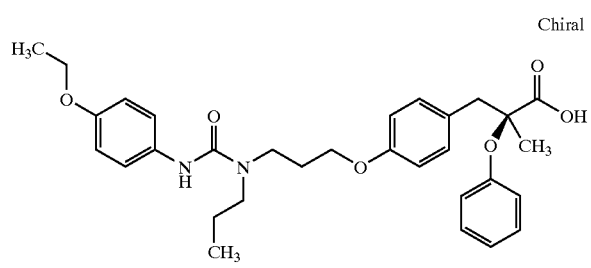
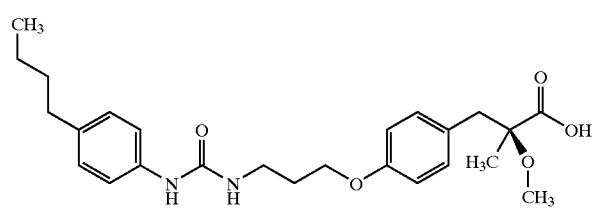
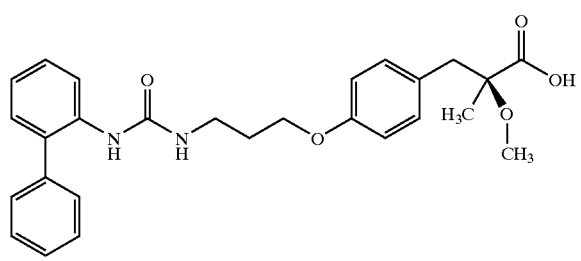
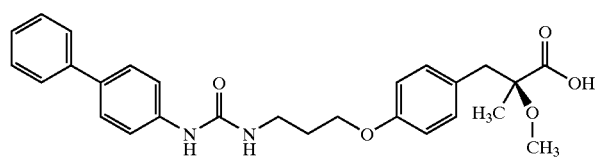

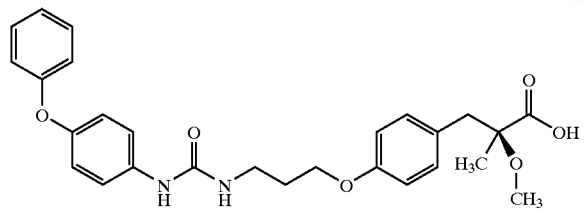
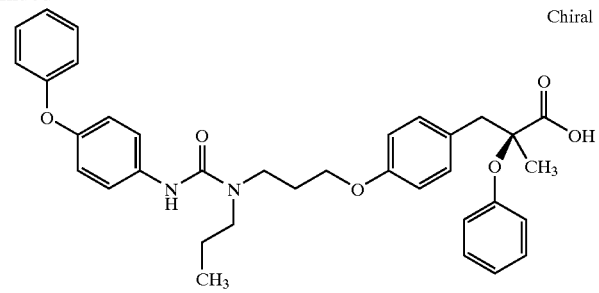
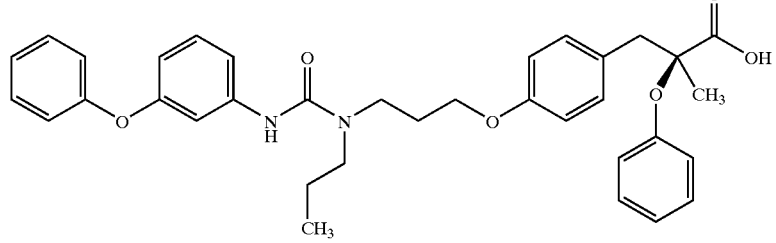
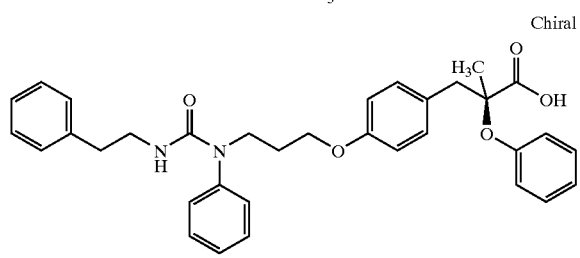
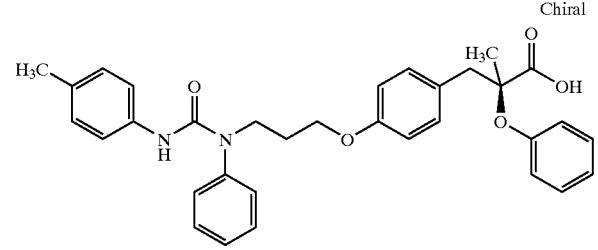
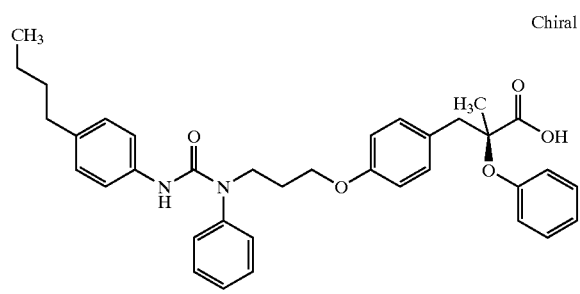
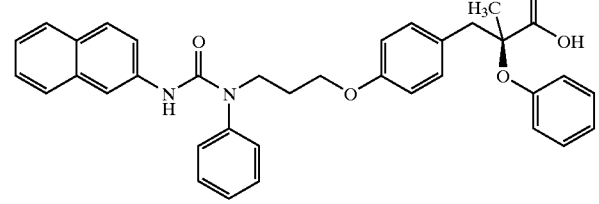
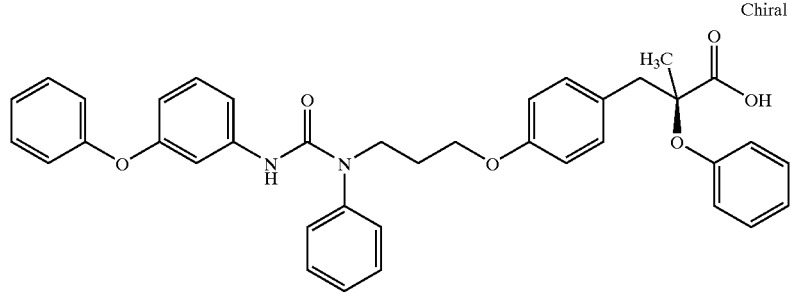
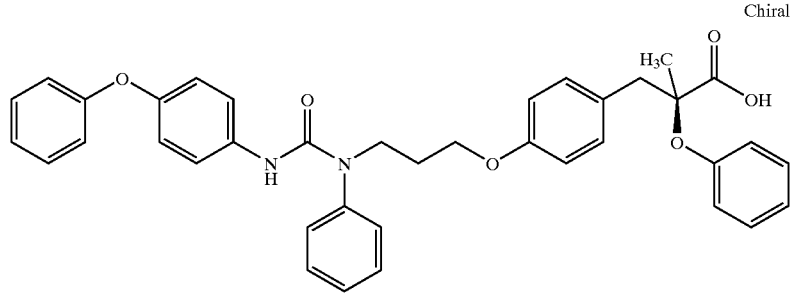

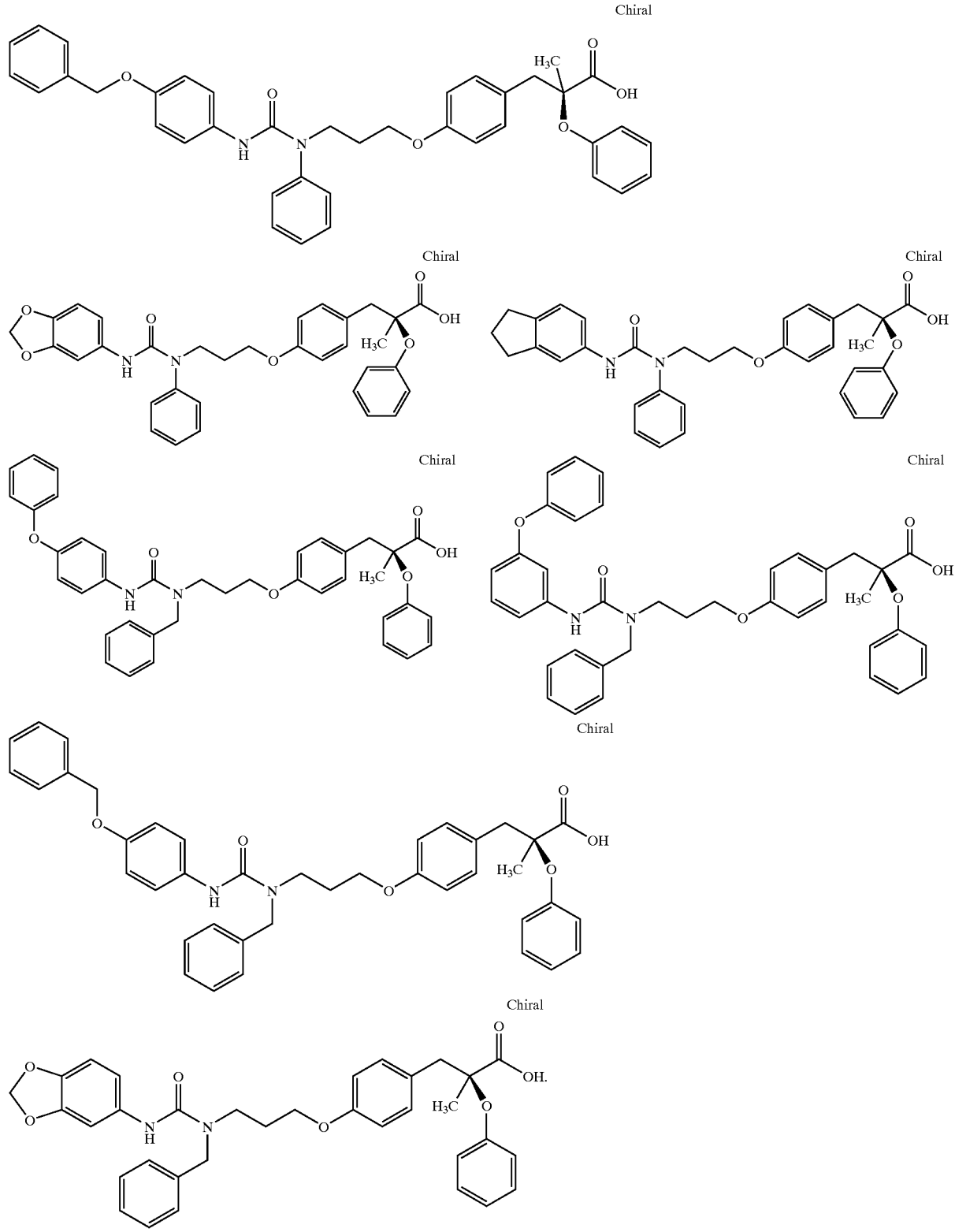

What is claimed is:

1. Compound of the structural formula I:

Formula I

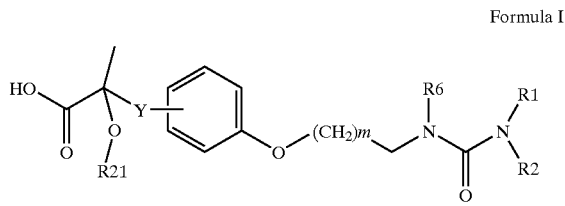

and pharmaceutically acceptable salts, solvates and hydrates thereof, wherein:
(a) R1, R2 and R6 are each independently selected from the group consisting of hydrogen. $C_1$–$C_8$ alkyl, substituted $C_1$–$C_8$ alkyl, aryl-$C_{0-4}$-alkyl, substituted aryl-$C_{0-4}$-alkyl, $C_3$–$C_6$ cycloalkyl, substituted $C_3$–$C_6$ cycloalkyl, heteroaryl-$C_{0-4}$-alkyl, substituted heteroaryl-$C_{0-4}$-alkyl, $C_3$–$C_6$ cycloheteroalkylaryl-$C_{0-2}$-alkyl, substituted $C_3$–$C_6$ cycloheteroalkylaryl-$C_{0-2}$-alkyl, $C_3$–$C_6$ cycloalkylaryl-$C_{0-2}$-alkyl and substituted $C_3$–$C_6$ cycloalkylaryl-$C_{0-2}$-alkyl; wherein the substituents for said substituted alkyl, arylalkyl, cycloalkyl, heteroarylalkyl, cycloheteroalkylarylalkyl, and cycloalkylarylalkyl are from one to three substituents each independently selected from R1';
(b) R1', R3', and R4' are each independently selected from the group consisting of H, C1–C5 alkyl, C1–C5 alkoxy, C1–C5 haloalkyl, C1–C5 haloalkoxy, nitro, cyano, CHO, hydroxyl, aryl$C_0$–$C_{5}$alkoxy, aryl$C_0$–$C_{5}$alkyl, alkylcarboxamido and COOH;
(c) Y is C, O, S, NH or a single bond;
(d) m is 0, 1, or 2; and
(e) R21 is selected from the group consisting of phenyl, substituted phenyl, and $C_1$–$C_6$ alkyl.

2. A compound as claimed by claim 1 wherein R6 is selected from the group consisting of hydrogen, substituted $C_1$–$C_4$ alkyl, $C_1$–$C_4$ alkyl, substituted aryl-$C_{0-4}$-alkyl, and aryl-$C_{0-4}$-alkyl.

3. A compound as claimed by claim 1 wherein Y is C.

4. A compound as claimed by claim 1 or claim 3 wherein aryl is substituted phenyl.

5. A compound as claimed by claim 4 wherein R2 is hydrogen and R1 is substituted phenyl.

6. A compound as claimed by claim 1 or 5 wherein substituted phenyl is substituted with a group selected from aryl, aryloxy, and arylalkyloxy.

7. A compound as claimed by claim 4 wherein the $CO_2C((CH_3)(OR21)$-Y group is in the para position in relation to the X linker.

8. A compound as claimed by claim 7 wherein R1 is selected from unsubstituted phenyl and substituted phenyl, and R6 is hydrogen.

9. A compound as claimed by claim 7 wherein R1 is substituted phenyl wherein the phenyl substituent is one or two independently selected from the group consisting of $CF_3$, $C_1$–$C_4$ alkyl, and halo.

10. A compound as claimed by claim 9 wherein R1 is substituted phenyl and R2 is hydrogen.

11. A pharmaceutical composition, comprising a pharmaceutically acceptable carrier and at least one compound as claimed by claim 1.

12. A method of modulating a peroxisome proliferator activated receptor, comprising the step of contacting the receptor with at least one compound as claimed by claim 1.

13. A method of treating diabetes mellitus in a mammal, comprising the step of administering to the mammal in need thereof, a therapeutically effective amount of at least one compound of claim 1.

14. A method of preventing diabetes mellitus in a mammal, comprising the step of administering to the mammal in need thereof, an effective amount of at least one compound of claim 1.

15. A method of treating Syndrome X in a mammal, comprising the step of administering to the mammal in need thereof, a therapeutically effective amount of at least one compound of claim 1.

16. A compound of claim 1 selected from the group consisting of: